United States Patent [19]
Kunimatsu et al.

[11] Patent Number: 6,090,268
[45] Date of Patent: Jul. 18, 2000

[54] CO GAS SENSOR AND CO GAS CONCENTRATION MEASURING METHOD

[75] Inventors: Keiji Kunimatsu; Hidemi Akita, both of Hokkaido, Japan

[73] Assignee: Imra Japan Kabushikikaisha, Japan

[21] Appl. No.: 08/981,624

[22] PCT Filed: Apr. 22, 1997

[86] PCT No.: PCT/JP97/01379

§ 371 Date: May 15, 1998

§ 102(e) Date: May 15, 1998

[87] PCT Pub. No.: WO97/40371

PCT Pub. Date: Oct. 30, 1997

[30] Foreign Application Priority Data

Apr. 22, 1996 [JP] Japan .................................. 8-124050

[51] Int. Cl.[7] .................................................. G01N 27/48
[52] U.S. Cl. .................. 205/782; 205/783.5; 204/421; 204/431
[58] Field of Search ................. 429/19, 22; 204/421, 204/424, 425, 426, 431, 432; 205/782, 783, 783.5

[56] References Cited

U.S. PATENT DOCUMENTS 4,729,824  3/1988  Giner ...................................... 204/415
5,712,052  1/1998  Kawatsu ................................... 429/13

*Primary Examiner*—T. Tung
*Assistant Examiner*—Jennifer C. McNeil
*Attorney, Agent, or Firm*—Lorusso & Loud

[57] ABSTRACT

A CO gas sensor according to the present invention includes a gas collecting container for collecting a measured gas therein; a detecting section provided within the gas collecting container and having at least a pair of electrodes positioned through electrolyte; and a voltage applying apparatus for applying voltage to the detecting section. One of the electrodes of the detecting section is a detection electrode having the capability of adsorbing at least one of hydrogenous gas and CO gas when a voltage is applied and then oxidizing it. By introducing a measured gas into a gas collecting container of the CO gas sensor and carrying out electrolysis according to a potential sweep method or a pulse method with the measured gas being in contact with the detecting section, a CO gas concentration in the measured gas can be measured based on an electrical current value obtained at the detecting section and changes of the electrical current with elapse of time. According to the CO gas sensor of the present invention, it is possible to accurately carry out detection and measurement of the concentration of CO gas when CO gas is to be detected or measured even in a gaseous atmosphere containing a relatively large amount of hydrogen gas and $CO_2$ gas.

16 Claims, 20 Drawing Sheets

CO GAS SENSOR AND CO GAS CONCENTRATION MEASURING METHOD

FIELD OF THE INVENTION

The present invention relates to a CO gas sensor for measuring the concentration of CO gas contained in a gaseous phase and to a method of measuring the concentration of CO gas, and in particular relates to a CO gas sensor for measuring the concentration of CO gas in a gaseous atmosphere containing relatively high concentrations of hydrogen gas and carbon dioxide gas, a fuel cell power generating apparatus equipped with such CO gas sensor, and a method of measuring the concentration of CO gas.

BACKGROUND ART

In many cases, hydrogen gas is used as a fuel gas for fuel cells. As such hydrogen gas, a hydrogen gas rich reforming gas which is obtained by reforming methanol or the like is used. When manufacturing such a reforming gas, a tiny amount of carbon monoxide (CO), namely several tens ppm to several hundred ppm, is present as impurities. For this reason, when such a reforming gas is used as a fuel gas for a fuel cell, the CO gas is adsorbed on the surface of the platinum catalyst of the fuel cell electrodes, thus hindering ionization of the hydrogen gas and lowering the output of the fuel cell. In order to take appropriate measures to counter such a problem caused by the CO gas, it is necessary to continuously monitor the concentration of CO gas in the reforming gas used in the fuel cell.

Conventionally, as for the most commonly used CO gas sensor, there are known a controlled potential analysis type CO gas sensor and a semiconductor type CO gas sensor. However, for the reasons given below, neither of these CO gas sensors is appropriate for detecting CO gas in a reforming gas.

Namely, the reforming gas contains hydrogen gas used as a fuel in the fuel cell for the amount of about 75% thereof. In comparison with this, the reforming gas contains a relatively tiny amount of CO gas as described above. Therefore, it becomes necessary to detect or measure CO gas in a hydrogen gas atmosphere containing a relatively large amount of hydrogen gas. However, in the case where the concentration of CO gas is measured in such a hydrogen gas rich atmosphere using these CO gas sensors, there is a problem that it is difficult to accurately detect (qualitative analysis) or measure (quantitative analysis) such CO gas with either type of CO gas sensor due to influence of the hydrogen gas rich atmosphere in which interference by hydrogen gas occurs.

In view of the problem mentioned above, it is an object of the present invention to provide a CO gas sensor which can accurately carry out detection (qualitative analysis) and measurement (quantitative analysis) of the concentration of CO gas when CO gas is detected or measured in a gaseous atmosphere containing a relatively large amount of hydrogen gas and carbon dioxide gas, a fuel cell power generating apparatus equipped with such a CO gas sensor, and a method of measuring the concentration of CO gas.

SUMMARY OF THE INVENTION

The present invention relates to a CO gas by the present inventors, the inventors have found a CO gas sensor and a method of measuring the concentration of CO gas which can accurately measure the concentration of CO gas contained in a mixture gas even if the mixture gas contains a relatively large amount of hydrogen gas and carbon dioxide gas while it contains a relatively tiny amount of CO gas and employs a measuring principle which is different from that of the conventional CO gas sensor.

Namely, a CO gas sensor according to the present invention is characterized by comprising: a gas collecting container for collecting a measured gas therein; a detecting section provided within the gas collecting container and having at least a pair of electrodes spaced apart in an electrolyte; and a voltage impressing apparatus for impressing voltage to said detecting section.

One of the electrodes of the detecting section of the CO gas sensor according to the present invention is characterized by a detection electrode having a characteristic for adsorbing at least one of hydrogen gas and CO gas when a voltage is impressing and then oxidizing it.

It is preferred that the detection electrode allows for diffusion of the measured gas into the electrode. For this gas diffusion means, for example a material formed of a porous carbon carrying a platinum catalyst can be used. Further, such a material can be used for the entire detection electrode or can be used as a gas diffusing layer formed on a surface portion of the detection electrode. The electrolyte of the detection section of the CO gas sensor according to the present invention can be selected from the group comprising electrolyte solution and solid electrolyte having an ionic conductivity.

Further, the CO gas sensor of the present invention can be incorporated into a fuel cell. Namely, in a fuel cell power generating apparatus comprising reforming material storing means for storing a reforming material, reforming means for reactively reforming the reforming material supplied from the reforming material storing means into a hydrogen gas rich reforming gas, and a fuel cell to which an oxidizer gas and the reforming gas produced by the reforming means are supplied to cause a cell reaction to output electrical power, the CO gas sensor and a CO gas eliminating apparatus are disposed between said reforming means and said fuel cell, thereby enabling a fuel cell power generating apparatus without any contamination by CO gas at a fuel electrode.

On the other hand, the CO gas sensor of the present invention has utilizations other than the use for a fuel cell. For example, it can be used in a manufacturing process of a hydrogen fuel and in a high concentration hydrogen atmosphere.

Further, a method of measuring a CO gas concentration according to the present invention is characterized by the steps of introducing a measured gas into a gas collecting container of the CO gas sensor; carrying out electrolysis by applying a potential in a controlled manner either in a potential sweep mode or in a pulsed mode method or a pulse method under the condition that the measured gas is in contact with a detecting section; and thereby measuring a CO gas concentration in the measured gas based on an electrical current value obtained at the detection electrode and changes of the electrical current with elapse of time.

BEST MODE FOR EMBODYING THE INVENTION

Figure 1:
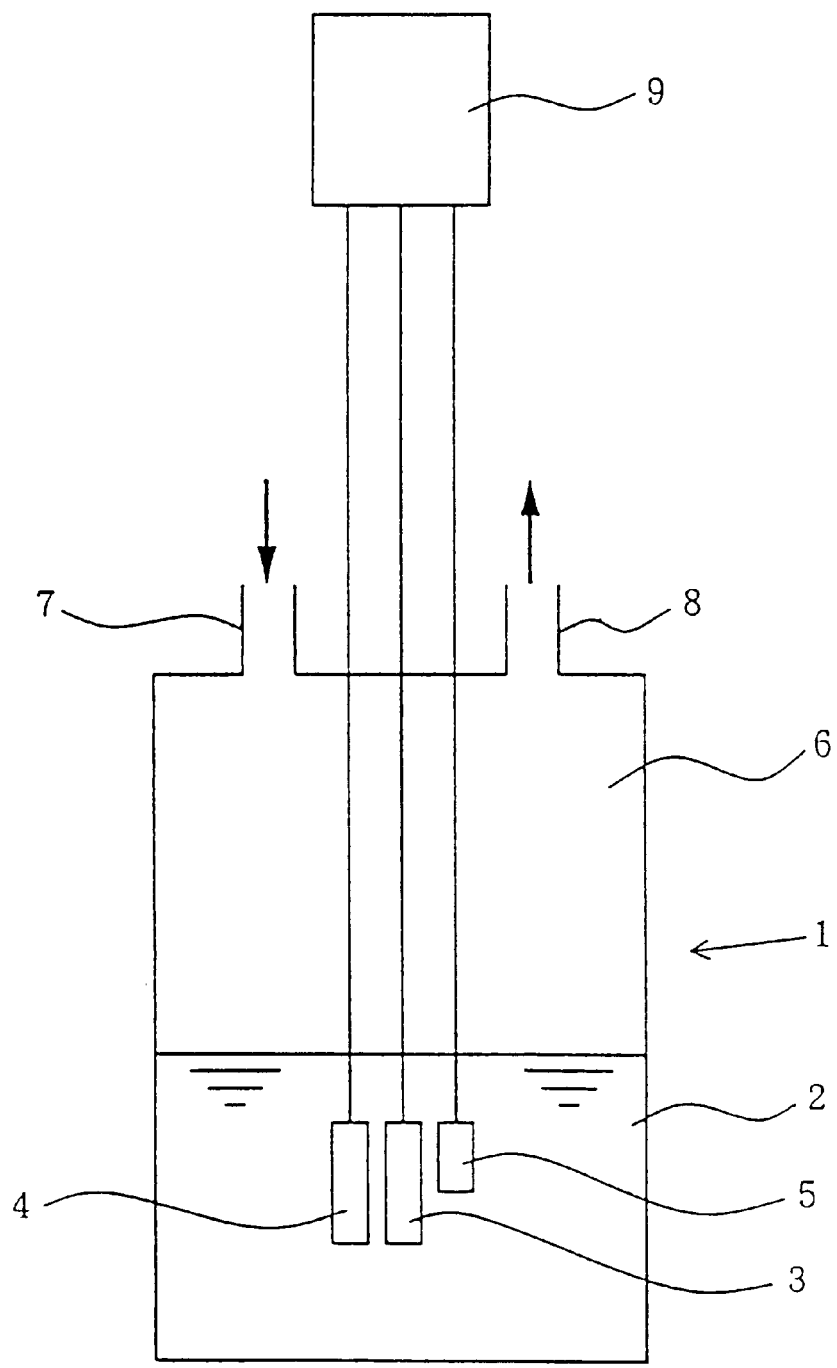
FIG. 1 is a schematic view for explaining a CO gas sensor according to the present invention in which a liquid-type electrolyte is used as an electrolyte (hereinafter, this type of gas sensor is referred to as "a wet type CO gas sensor").

FIG. 1 is a schematic view of a CO gas sensor of the present invention, in which a liquid electrolyte is used as an electrolyte (hereinafter, this type of the CO gas sensor is referred to as "a wet type CO gas sensor"). In this drawing, the reference numeral 1 denotes a CO gas sensor. In the inside of the CO gas sensor 1, there is a chamber for holding an electrolyte solution 2. This chamber also has a role as a gas collecting space 6 through which a gas is to measure its concentration of CO. Immersed in the electrolytic solution 2 are a detection electrode 3, a counter electrode 4 which is disposed so as to face the detection electrode 3, and a reference electrode 5. Provided outside the gas purging space 6 is a voltage impressing apparatus 9, such as a potentiostat or the like, for impressing a voltage to the electrodes. Further, the CO sensor 1 is provided with an inlet port 7 for introducing a measured gas and an outlet port 8 for expelling the measured gas.

Figure 2:
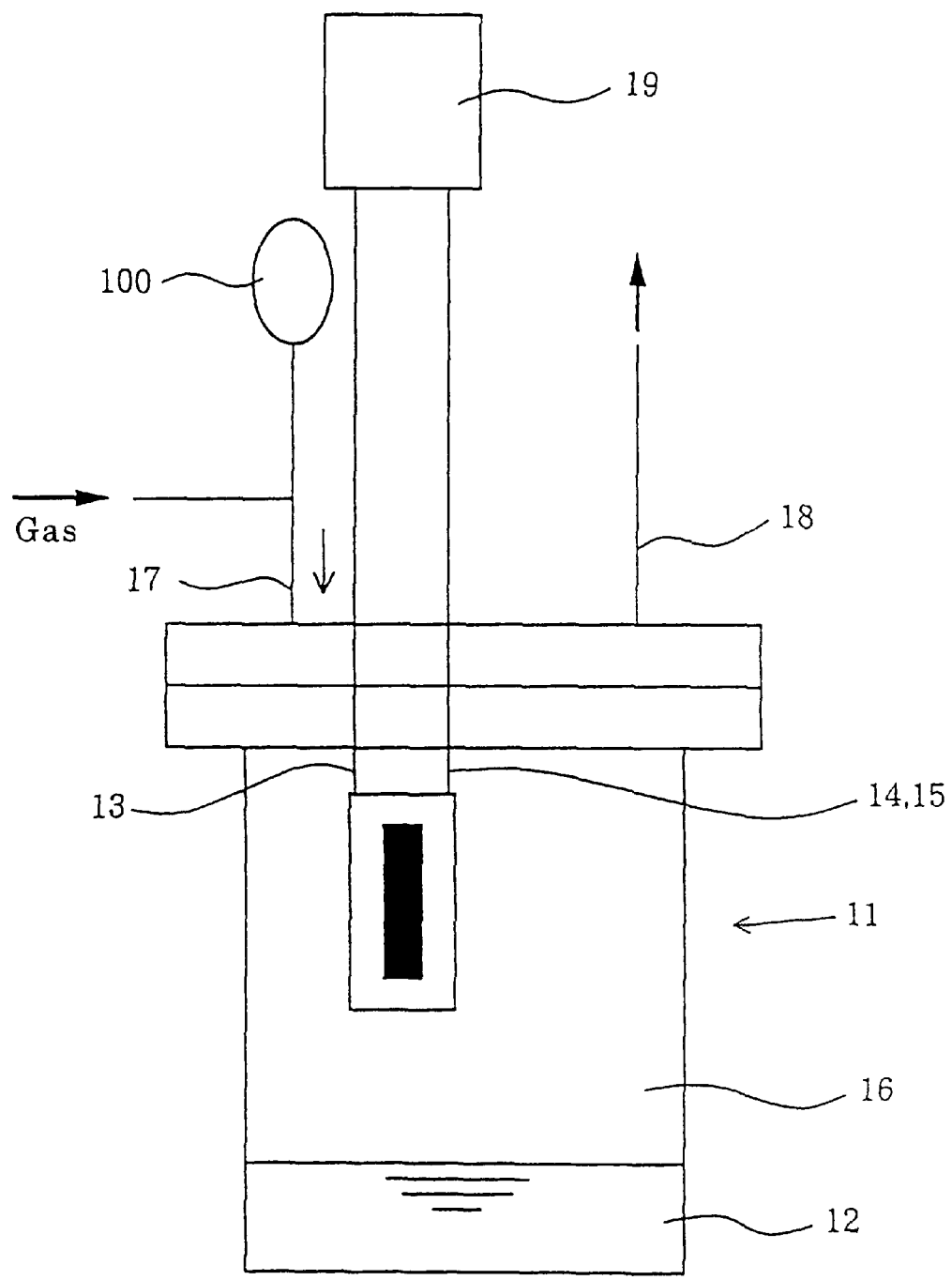
FIG. 2 is another schematic view for explaining another CO gas sensor according to the present invention which is different from the gas sensor shown in FIG. 1, in which a solid electrolyte membrane such as NAFION (registered trademark of DuPont Co.) is used as an electrolyte (hereinafter, this type of gas sensor is referred to as "a dry type CO gas sensor").
Figure 3:
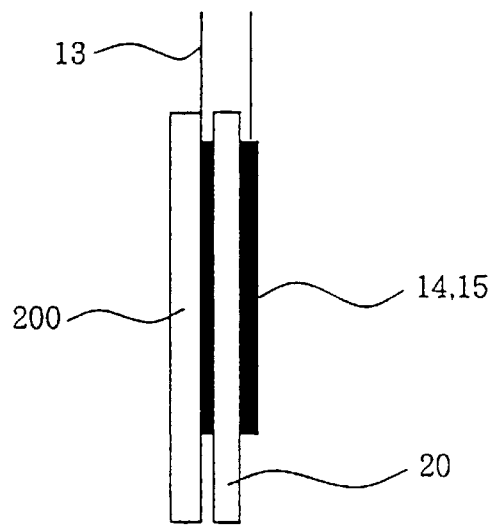
FIG. 3 is a sectional view of each electrode of the dry type CO gas sensor shown in FIG. 2, in which a gas diffusion layer formed from a porous film or liquid membrane is disposed between the electrode and a measured gas.
Figure 4:
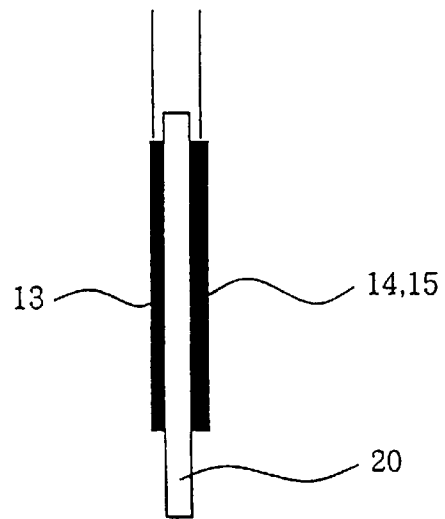
FIG. 4 is a sectional view of each electrode of the dry type CO gas sensor shown in FIG. 2, in which there is no gas diffusion layer as shown in FIG. 3.

FIG. 2 is a schematic view of another CO gas sensor which is different from the gas sensor shown in FIG. 1, in which a solid electrolyte membrane such as NAFION (registered trademark of DuPont Co.) is used as an electrolyte (hereinafter, this type of gas sensor is referred to as "a dry type CO gas sensor"). Further, FIGS. 3 and 4 are cross-sectional views of two types of electrode portions used for the dry type CO gas sensor shown in FIG. 2. The special feature of the dry type CO gas sensor shown in FIG. 3 resides in the provision of a gas diffusion layer 200 between the detection electrode and the measured gas, and the special feature of the dry type CO gas sensor shown in FIG. 4 is the absence of such a gas diffusion layer.

In the case of the dry type CO gas sensor which does not use a liquid for the electrolyte, when the detecting electrode 13 is in direct contact with a measured gas containing a large amount of hydrogen, a high electric current flows due to hydrogen ionization reactions, so that it becomes impossible to detect the quantity of electricity involved in oxidizing the CO adsorbed on the detecting electrode 13. For this reason, as shown in FIG. 3, a gas diffusion layer 200 formed from a porous membrane or a liquid membrane which is several micrometers to several millimeters in thickness is provided between the detecting electrode 13 and the measured gas in order to control the diffusion of hydrogen, and this makes it possible to use the same quantitative method employed for the wet type CO gas sensor.

Further, in the case like that shown in FIG. 4 where there is no provision of a gas diffusion layer 200 shown in FIG. 3, because the hydrogen ionization current is hindered by the adsorption of CO, it is possible to indirectly determine the quantity of CO from changes in the hydrogen ionization current with lapse of time at the CO adsorption potential.

In FIG. 2, the reference numeral 11 denotes a CO gas sensor. In this CO gas sensor 11, there is a chamber which holds a quantity of water 12 for maintaining humidified conditions inside thereof. This chamber also serves as gas collecting container 16 in which a measured gas is introduced to measure its concentration of CO. Arranged in the gas collecting container 16 are a detection electrode 13 made of a platinum mesh or the like, a counter electrode 14 which is disposed so as to face the detection electrode 13, and a reference electrode 15, which are laminated with each other. Provided outside the gas collecting container 16 is a voltage impressing apparatus 19, such as a potentiostat or the like, for impressing a voltage on each of the electrodes. Further, the CO sensor 11 is provided with an inlet port 17 for introducing a measured gas and an outlet port 18 for expelling the measured gas. Furthermore, a pressure regulating device 100 is connected to the inlet port 17 for regulating the pressure inside the CO gas sensor 11.

FIGS. 3 and 4 are cross-sectional views of a portion of the solid polymer electrolyte membrane and each of the electrodes shown in FIG. 2, in which the solid polymer electrolyte membrane 20 forms a laminated structure with the detection electrode 13 and either the reference electrode 15 or the counter electrode 14.

Each of the electrodes of the wet type CO gas sensor and the dry type CO gas sensor may be provided with a gas diffusion layer 200 formed from either a porous membrane or liquid membrane to diffuse the measured gas into the electrodes in order to more efficiently adsorb and oxidize CO with the electrodes. On the other hand, for shortening a response time of the CO gas sensor, it is possible to either make the gas diffusion layer 200 very thin or omit the gas diffusion layer 200.

In the CO gas sensors according to the present invention, sulfuric acid solution is preferably used for the liquid electrolyte, and a membrane such as NAFION (a registered trademark of DuPont, Co.) is preferably used for the solid electrolyte membrane.

As for the electrode material used for constructing the electrodes of the CO gas sensor of the present invention, any metal can be used if it can adsorb either hydrogen or CO or both hydrogen and CO within an appropriate potential range and has the capability to electrochemically oxidize them; examples including Pt, Au, Cu, Ni, Pd, Ag, Rh, Ru or any alloys containing one or more of these metals.

In measuring the concentration of CO in a measured gas using one of the CO gas sensors described above, a measured gas is introduced into the inside of the CO gas sensor, whereupon the measured gas comes into contact with a detection electrode inside the CO gas sensor, and then electrolysis is carried out by a potential regulating method, thereby measuring the concentration of CO gas in the measured gas from the obtained current value and changes of the current with elapse of time.

Examples of the potential regulating method which can be used in the present invention include a cyclic voltammetry method and a pulse method and a combination thereof. The feature of the cyclic voltammetry method is to carry out potential sweep with a triangle wave, and the feature of the pulse method is to apply a pulsed potential continuously between two potentials. The following embodiments are described with reference to the cases according to the cyclic voltammetry method and the pulse method.

EMBODIMENT 1

The embodiment 1 is an example which is carried out according to the cyclic voltammetry method.

Figure 5:
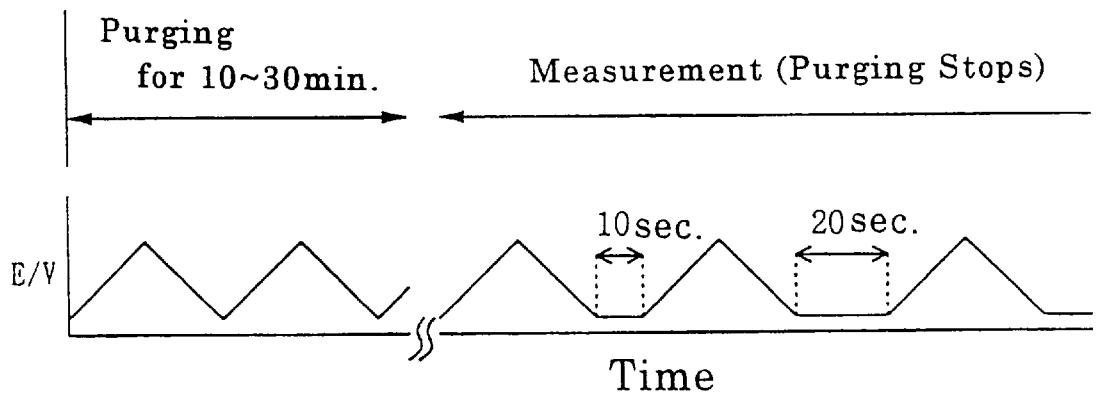
FIG. 5 is a graph which shows one example of the relationship between a voltage applying time and an applied voltage according to the cyclic voltammetry method using the wet type CO gas sensor.

In the case where the CO gas concentration is measured with the wet type CO gas sensor, a measured gas is purged until the electrolytic solution (e.g., 0.5 M $H_2SO_4$) is saturated with the measured gas, and once the concentration of CO gas which is in contact with the surface of the detection electrode inside the CO gas sensor becomes stable, a cyclic voltammogram is generated using the cyclic voltammetry method in which the applied voltage is scanned. It takes about several ten minutes to carry out purging with the wet type CO gas sensor since it takes a certain time to saturate the electrolyte solution with a fuel gas. In this connection, FIG. 5 shows one example of the voltage applying time, applied voltage and holding time achieved by a cyclic voltammetry method using this wet type CO gas sensor.

In the case where the dry type CO gas sensor is used to measure the concentration of CO gas, the measured gas comes into direct contact with the electrodes. Therefore, it is not necessary to carry out purging of the measured gas for long time as when using the wet type CO gas sensor, and it only takes from roughly several tens of seconds to several minutes for the concentration of the measured gas to be stabilized. As a result, after the measured gas has been introduced, it becomes possible to quickly measure the concentration of CO in the measured gas by means of the cyclic voltammetry method mentioned above. Accordingly, in the case where a solid polymer electrolyte membrane is used as a CO gas sensor for controlling the supply of a fuel gas in a fuel cell, the response time is shorter in comparison with the wet type CO gas sensor, which means that the dry type CO gas sensor has excellent quick-response characteristics when used as a CO gas sensor for fuel cells.

In the case where the CO gas sensors shown in FIGS. 1 and 3 are used, the relationship between the CO concentration and either the quantity of CO adsorbed on the detection electrode or the amount of electricity at the time of oxidizing the CO can be calculated from the cyclic voltammogram to produce an analytical curve, thereby performing the quantitative determination of CO. The concentration of CO in the measured gas can be determined directly from the value of the area (coulomb) at the peak of the electric current by which the adsorbed CO is oxidized, or it can be determined indirectly based on the CO adsorption coverage $\Theta_{CO}$ obtained from the current reduction because reduction of the ionization current of the adsorbed hydrogen atom is caused by the adsorption of CO on the detection electrode, thereby detecting the CO concentration in the measured gas. Namely, based on the difference between $Q_H$ which is the amount of electricity by the adsorbed hydrogen when the entire surface of the detection electrode is completely covered with adsorbed hydrogen atoms, and $Q_{H-CO}$ which is the amount of electricity due to oxidation of the adsorbed hydrogen when a part of the surface of the detection electrode adsorbs CO, it is possible to calculate the CO adsorption coverage $\Theta_{CO}$ from the method represented by the Formula (1) below.

$$\Theta_{CO} = 1 - Q_{H-CO}/Q_H \quad \text{Formula (1)}$$

Figure 6:
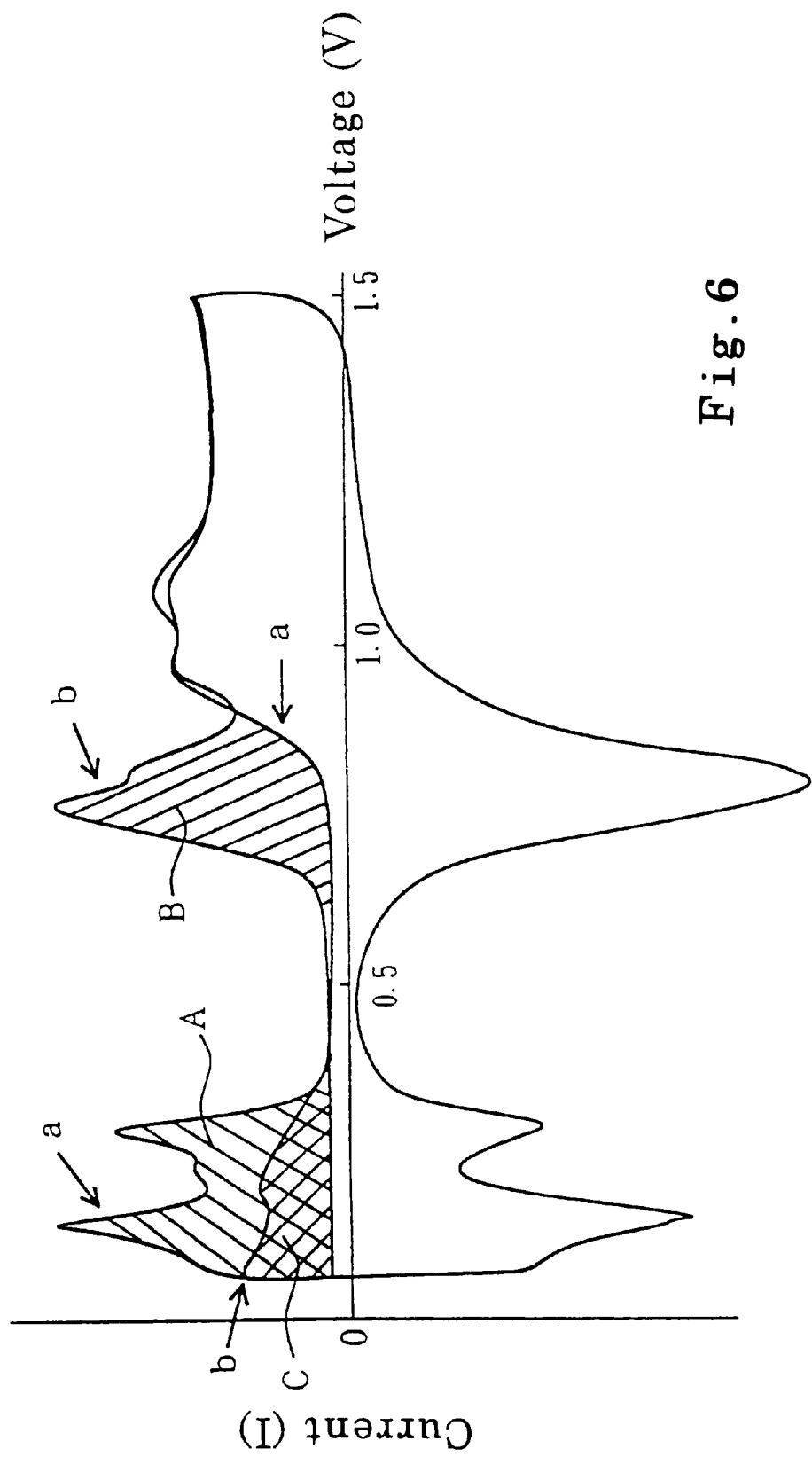
FIG. 6 is a graph which shows the cyclic voltammogram when a mixture gas containing 75% hydrogenous gas, 24% carbon dioxide and 1% carbon oxide (CO) is purged, in which the curve "a" indicates the case where a potential scanning is carried out continuously without causing CO to be adsorbed and the curve "b" indicates the case where a potential scanning is carried out after the voltage has been kept at 0.4 V which is a voltage that allows CO to be adsorbed for 180 seconds.

Formula (1) above will now be explained by the graph shown in FIG. 6. FIG. 6 is a graph which shows the cyclic voltammogram when a gas mixture containing 75% hydrogen, 24% carbon dioxide and 1% carbon oxide (CO) is introduced, in which the curve "a" indicates the case where a potential scanning is carried out continuously without causing CO to be adsorbed and the curve "b" indicates the case where a potential scanning is carried out after the voltage has been kept at 0.4 V which is a voltage that allows CO to be adsorbed for 180 seconds.

In FIG. 6, the curve "a" in the potential between 0.05 V and 0.3 V shows the flow of an electric current due to an oxidation reaction of the adsorbed hydrogen atoms, as indicated by Formula (2) below.

$$H \rightarrow H^+ + e^- \quad \text{Formula (2)}$$

In the curve "b", the electric current due to oxidization of the adsorbed hydrogen becomes less than that in the curve "a" due to the adsorption of CO, but at the same time an electric current flows in the potential between 0.65 V and 1.0 V due to an oxidation reaction being caused by the adsorbed CO, as indicated by Formula (3) below.

$$CO + H_2O \rightarrow CO_2 + 2H^+ + 2e^- \quad \text{Formula (3)}$$

In this connection, the potentials detected by the cyclic voltammogram at which the adsorbed hydrogen is oxidized and oxidation reactions occur for the adsorbed CO will differ depending on the electrode material used in the CO gas sensor. In FIG. 6, the quantity of electricity $Q_{CO}$ due to oxidation of CO is represented by the oblique line area B. On the other hand, the quantity of electricity $Q_H$ which is complete oxidation of the adsorbed hydrogen on the detection electrode observed when no CO is adsorbed on the detection electrode is represented by the total combined area of the oblique line area A and the net-shaped area C. Further, the quantity of electricity $Q_{H-CO}$ due to oxidation of the adsorbed hydrogen for the case in which a portion of the Pt surface has adsorbed CO is represented by the net-shaped area C. In this connection, the elctricities represented by the oblique line area A and the oblique line area B are identical to the amount of CO adsorbed, which are one electron reaction when the above described Formula (2) is used and two electron reactions when the above described Formula (3) is used, respectively, so that their ratio becomes 1:2.

Figure 7:
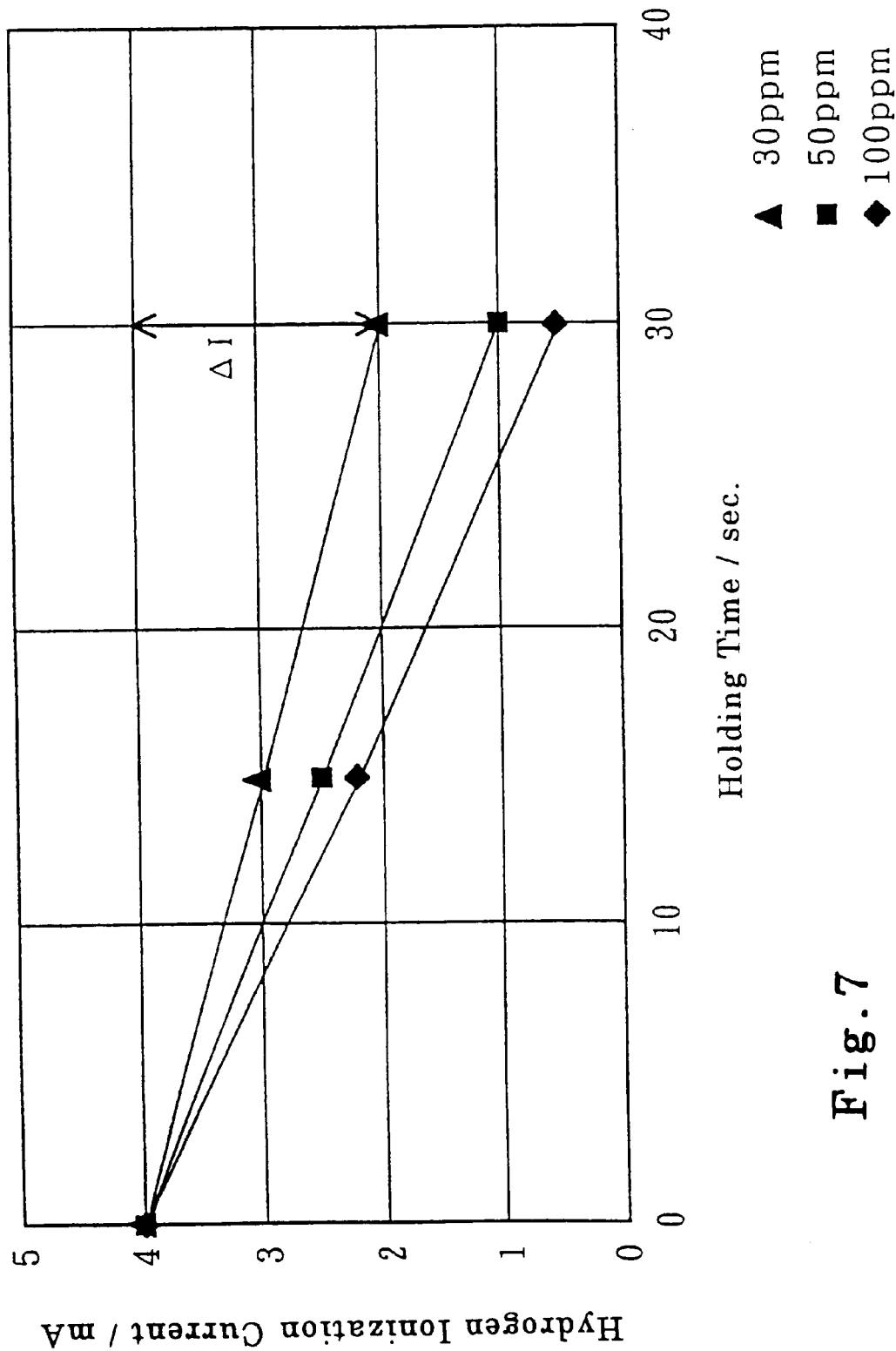
FIG. 7 is a graph which shows changes of a hydrogen ionization current with elapse of time depending on the CO concentration when the dry type CO gas sensor shown in FIG. 4 is used.

In the case where the CO gas sensor shown in FIG. 4 is used, the relationship between the CO gas concentration and the decreased amount of hydrogen ionization current due to the adsorption of CO on the detection electrode 13 can be calculated to produce an analytical curve, thereby performing quantitative measurement of CO. The quantitative method of this sensor will now be described with reference to FIG. 7. In this respect, FIG. 7 is a graph which shows changes of a hydrogen ionization current with respect to elapse of time depending on the CO concentration when the dry type CO gas sensor shown in FIG. 4 is used. The hydrogen ionization current in this CO gas sensor decreases by an exact amount $\Delta I$ from an initial current value $I_o$ just after the voltage of the detection electrode has been controlled to oxidize and eliminate CO to a later value $I_t$ by holding the potential at which CO can adsorb for a predetermined time. Because $\Delta I$ gets becomes larger as the concentration of CO in the purged gas increases, it is possible to carry out quantitative measurements by calculating the relationship between $\Delta I$ and the concentration of CO in advance.

Furthermore, in order to improve the CO gas detection accuracy and detection sensitivity, it is necessary to positively carry out a transfer of the measured gas to the detection electrode, which can be carried out, for example, by controlling the flow of the measured gas. Further, in addition to this, in the case where the electrolyte is a liquid electrolyte, it is possible to either move or rotate the detection electrode or move the liquid electrolyte at a prescribed speed.

Further, in the case where a gas mixture contains $CO_2$ gas in addition to hydrogen gas and CO gas, such as a methanol reformation gas, the $CO_2$ gas will be reduced by the adsorbed hydrogen atoms at the CO gas adsorption potential of 0.05 V, thus creating more CO gas, and this results in a critical bar for detecting the CO gas originally contained in the measured gas. For this reason, it is necessary to set the CO gas adsorption potential so as to prevent the reduction of $CO_2$ gas and the oxidation of CO gas. For example, in the case where the detection electrode is made from Pt, the CO gas adsorption voltage should be around 0.4 V (RHE).

In this connection, it should be noted that even though the above embodiment is described for detecting the concentration of CO gas, the present invention is not limited to this embodiment. It is possible to use the principle of the present invention not only for the measurement of the concentration of CO gas but also for the measurement of the concentration of $CO_2$ gas if the holding potential is set to the $CO_2$ gas reduction potential.

Figure 8:
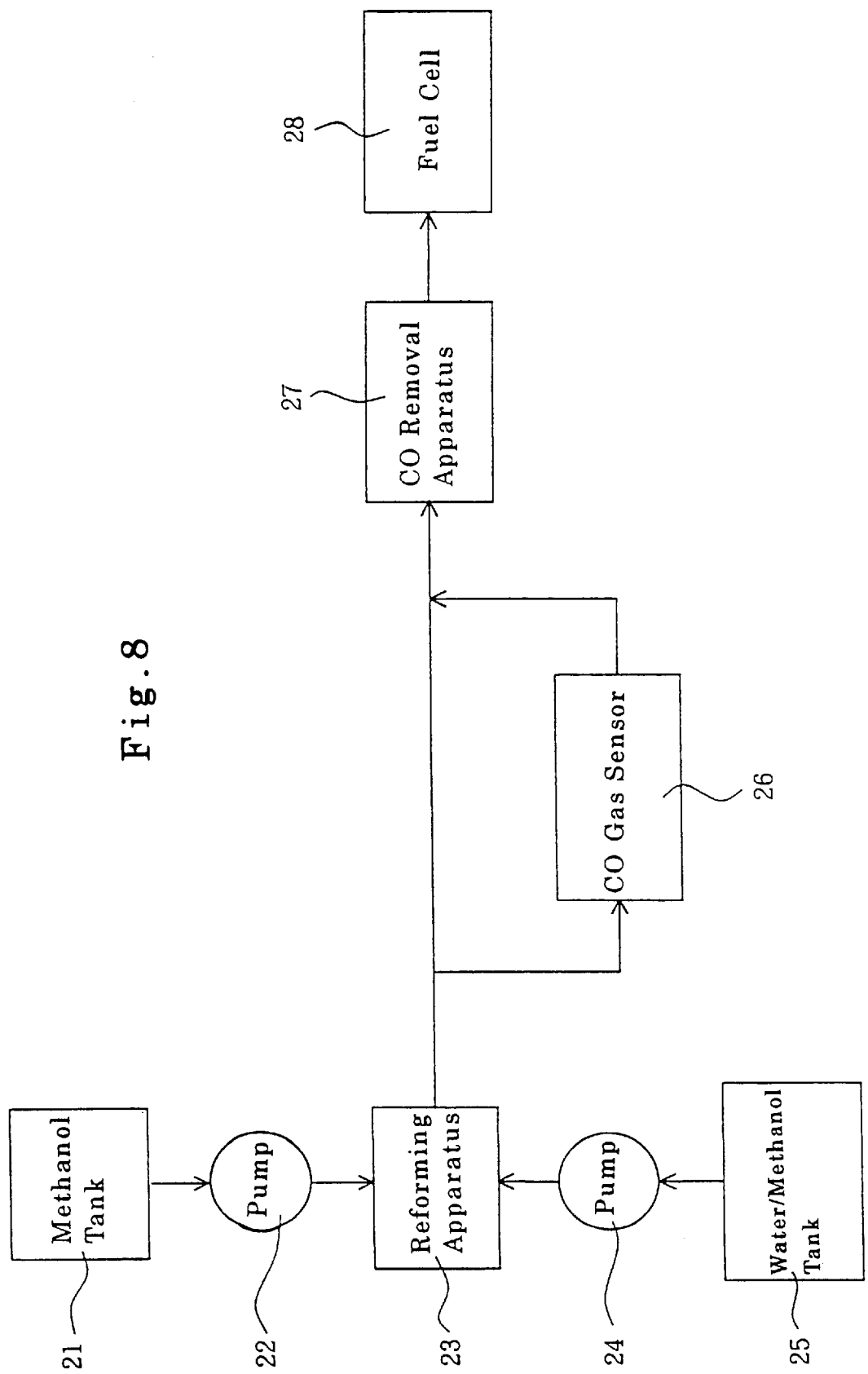
FIG. 8 is a block diagram which shows the example where the CO gas sensor according to the present invention is incorporated into a fuel cell system in which a reforming gas using a methanol as a source material is employed as a hydrogen gas fuel.

Next, FIG. 8 shows an example of a fuel cell system which is equipped with the CO gas sensor according to the present invention, in which a reformation gas obtained from methanol is used as a hydrogen gas fuel. In the fuel cell system shown in FIG. 8, methanol as a source material is introduced from a methanol tank 21 to a reforming apparatus 23 by means of a pump 22, and at the same time, water/methanol as a source material is introduced from a water/methanol tank 25 to the reforming apparatus 23 by means of a pump 24, whereby a reformation process creates a reformed gas containing roughly 75% hydrogen gas. Then, while a portion of such gas is being examined by the CO gas sensor 26 to measure the concentration of CO contained therein, the reformed gas undergoes a CO removal treatment in a CO removal apparatus 27 to remove CO, thereby the CO-free gas then being supplied to the fuel cell 28 as a hydrogenous gas fuel.

Next, the following experiments were carried out to examine the adsorption and oxidation of CO on the detection electrode in a methanol reformed gas atmosphere (containing 75% $H_2$ and 25% $CO_2$, and the respective CO concentrations are indicated as ppm) to determine whether or not it is possible to carry out quantitative measurement for the CO concentration.

Preparation of the Analytical Curves (1) In a wet type CO gas sensor, an electrolyte (0.5 M $H_2SO_4$) which is saturated with model gases having the CO concentrations of 100, 500, 1000 ppm, respectively, was subjected to a continuous cyclic voltammetry at a voltage of 0.05–1.50 V. In a dry type CO gas sensor, the same operation was carried out to saturate solid polymer electrolyte membrane such as NAFION (registered trademark of DuPont Co.).

(2) Then, a cyclic voltammogram (CV) of the detection electrode was obtained. From the obtained CV curve, the H oxidation wave was detected in the range 0.05–0.3 V and the CO oxidation wave was detected in the range 0.65–1.0 V.

(3) After the measurement for one CV cycle, the voltage was held at 0.4 V (for a holding time of 10–1800 seconds) to adsorb CO onto the detection electrode. The above processes were then repeated while changing the voltage holding time. Then, using the amount of decrease of the H oxidation wave and the amount of increase of the CO oxidation wave in these various CV curves, the CO adsorption coverage or the amount of CO oxidation current (C) were calculated.

(4) Then, the steps (1)–(3) were then repeated for all model gases (i.e., for the model gases having the CO concentrations of 100, 500 and 1000 ppm, respectively).

Figure 9:
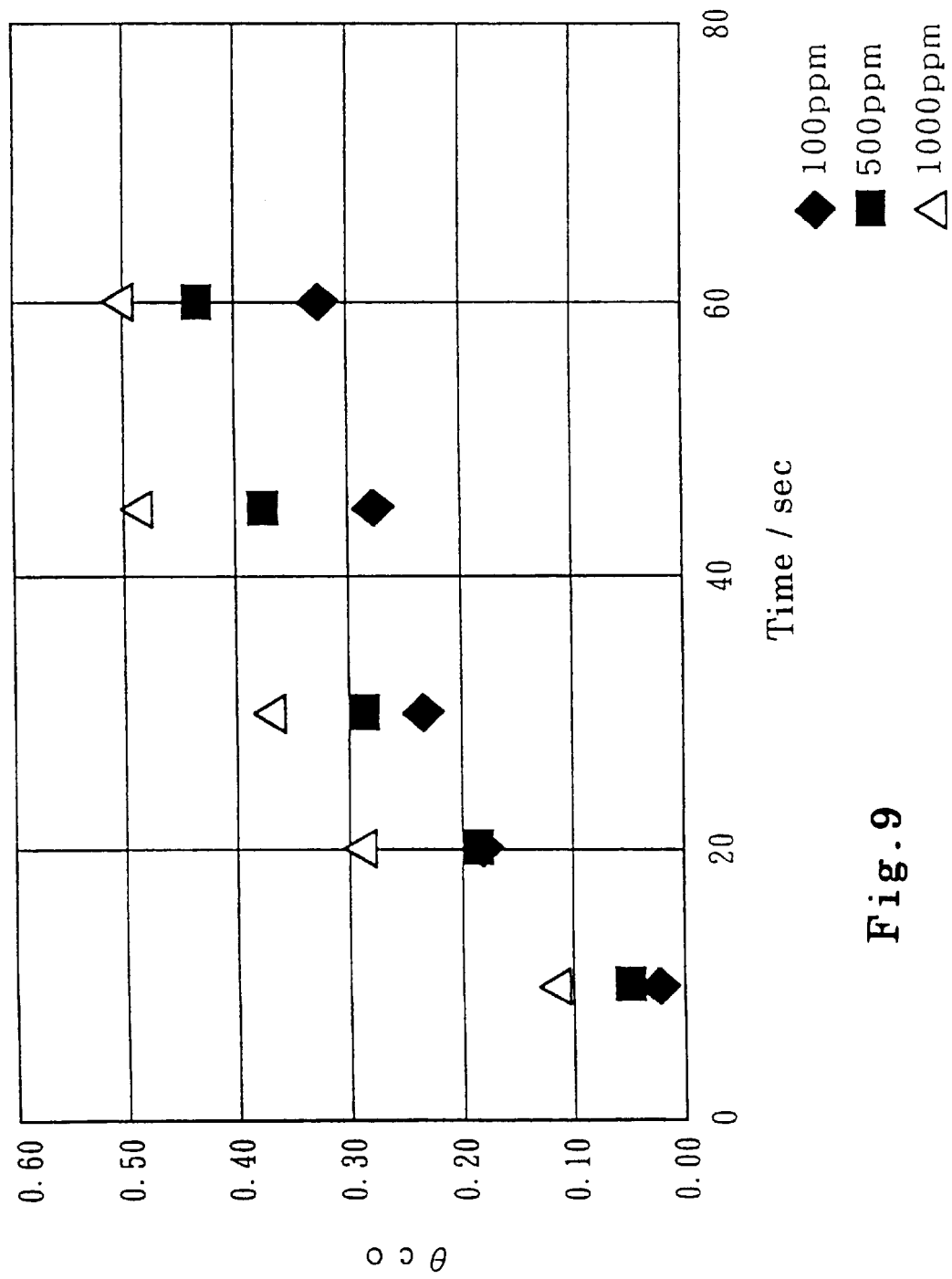
FIG. 9 is a graph which shows the relationship between the CO adsorption coverage $\Theta_{CO}$ (or quantity of electricity by CO oxidation) and the CO concentration with respect to the respective CO adsorption times when the wet type CO gas sensor of the present CO adsorption invention is used.
Figure 10:
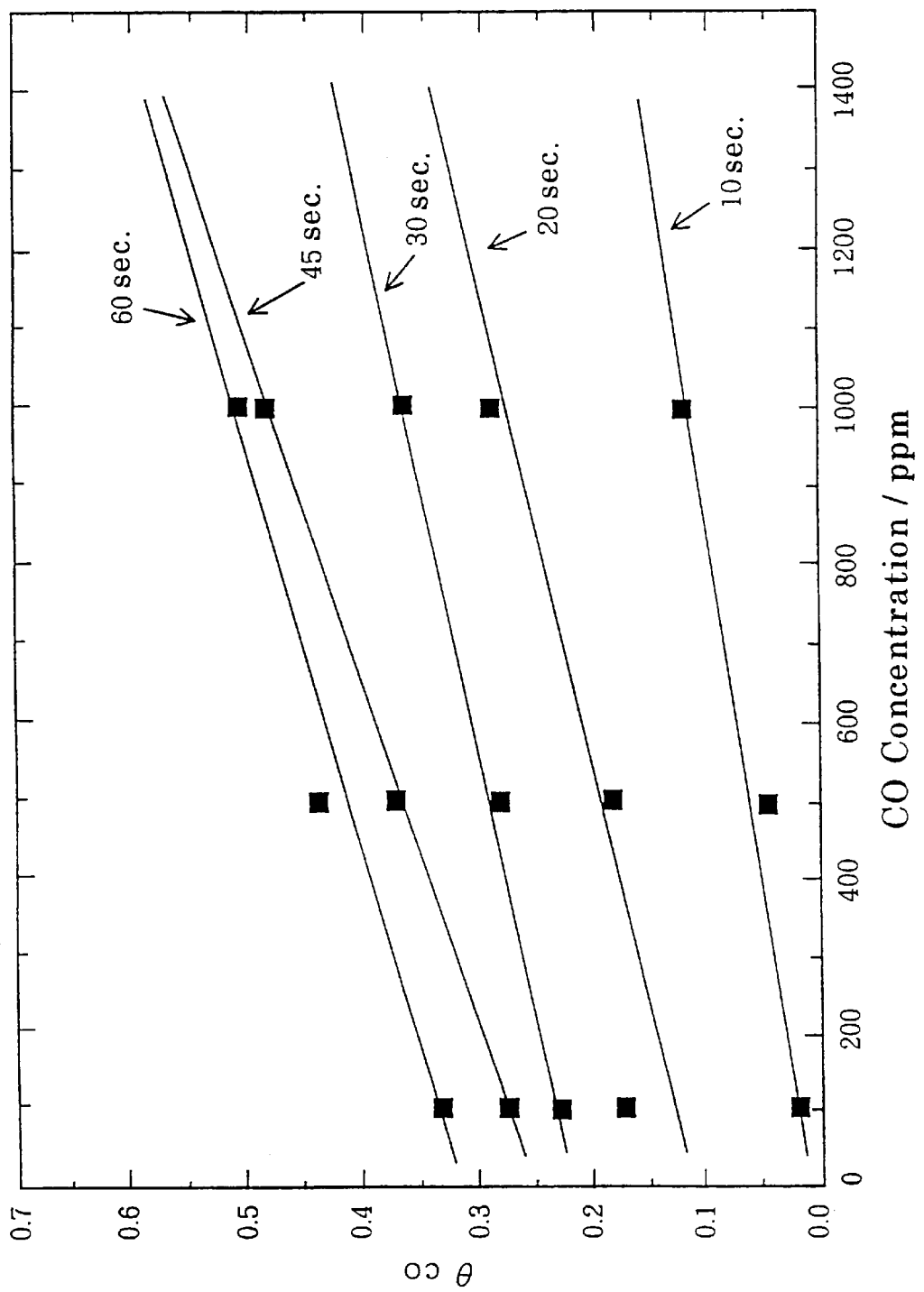
FIG. 10 shows a graph which is obtained by converting the $\Theta_{CO}$—time curve in FIG. 9 such that the CO adsorption coverage is plotted on the vertical axis while the CO concentration is plotted on the horizontal axis.

(5) Then, for the respective (CO adsorption) holding times, analytical curves which show the relationship between the CO concentrations and the CO adsorption coverage $\Theta_{CO}$ (or the amount of CO oxidation current) in the case where the wet type CO gas sensor was used were obtained. These results are shown by the graphs in FIG. 9. In FIG. 9, the mark ♦ designates a CO concentration of 100 ppm, the mark ■ designates a CO concentration of 500 ppm, and the mark Δ designates a concentration of 1000 ppm. According to FIG. 9, the CO adsorption coverage $\Theta_{CO}$ increases in a roughly linear manner with respect to lapse of the holding time, and the CO adsorption coverage $\Theta_{CO}$ becomes higher as the CO concentration of CO becomes higher. In this connection, FIG. 10 shows a graph which is obtained by converting the $\Theta_{CO}$—time curve in FIG. 9 such that the CO adsorption coverage $\Theta_{CO}$ is plotted on the vertical axis while the CO concentration is plotted on the horizontal axis.

Measuring the CO concentration in the Reformation Gas

After carrying out the operations described in (1) and (2) above on samples of reformation gases, CV measurements were conducted after a desired holding time, thereby obtaining the CO adsorption coverage $\Theta_{CO}$ (or the amount of CO oxidation current). In this way, it is possible to obtain the CO concentration (ppm) from the analytical curve corresponding to the $\Theta_{CO}$—CO concentration curve in the case where the wet type CO gas sensor shown in FIG. 10 is used.

Figure 11:
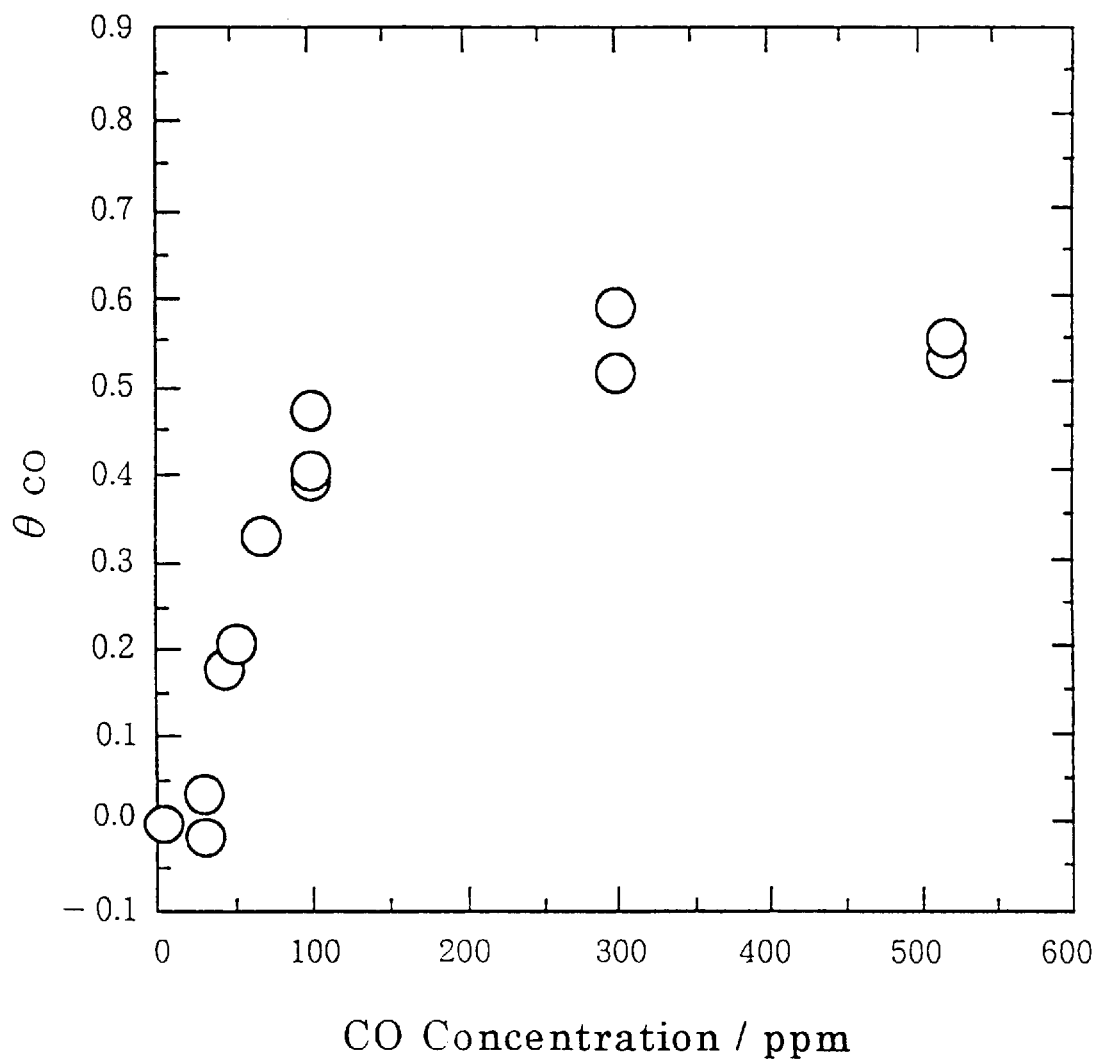
FIG. 11 is a graph which shows analytical curves of the relationship between the $\Theta_{CO}$ and the CO concentration, which are obtained under the condition that the CO adsorption time is set to be 30 seconds using the dry type CO gas sensor according to the present invention.

On the other hand, the same operations described in (1) and (2) above were carried out for a dry type CO gas sensor which uses a NAFION membrane as the electrolyte membrane. Thereafter, CV measurements were carried out at a prescribed CO adsorption holding time (e.g., 30 seconds), thereby obtaining the CO adsorption coverage $\Theta_{CO}$. In the case where such a dry type CO gas sensor is as used, it was possible to obtain analytical curves which show the relationship between the CO adsorption coverage $\Theta_{CO}$ and the CO concentration as shown in FIG. 11.

EMBODIMENT 2

Embodiment 2 relates to a method of measuring the CO concentration based on an analytical curve obtained by a pulse method (also known as a potential step method or pulse voltammetry method). This pulse method is another example of the potential regulating method, but it is different from the first embodiment in that potential is applied in a pulse like manner instead of the potential sweep at a predetermined speed performed in the first embodiment. Except for this difference, the structure of the apparatus of the second embodiment is the same as the structure of the apparatus of the first embodiment.

Examples of the analytical curves for determining the CO concentration according to the pulse method of the second embodiment include a general purpose analytical curve, a Langmuir type CO adsorption analytical curve, an analytical curve obtained from the relationship between the CO concentration and the inverse of the time required for reaching a predetermined electric current reduction rate, and an analytical curve obtained from the relationship between the CO concentration and the electric current reduction rate. In this embodiment, a measurement of the CO concentration can be carried out using any of these analytical curves. The principle for measuring the concentration of CO for these four types of analytical curves will now be described.

1. Method Using General Purpose Analytical Curve

Figure 12:
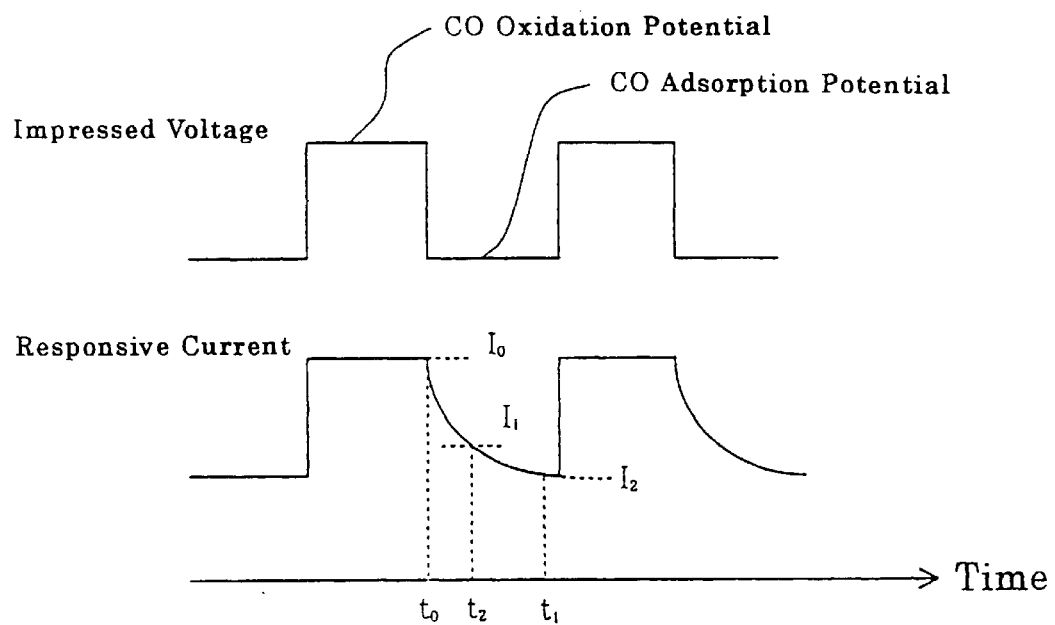
FIG. 12 is a graph which shows changes of a responsive current with elapse of time when a CO oxidation potential and a CO adsorption potential are applied in a pulse like manner.
Figure 13:
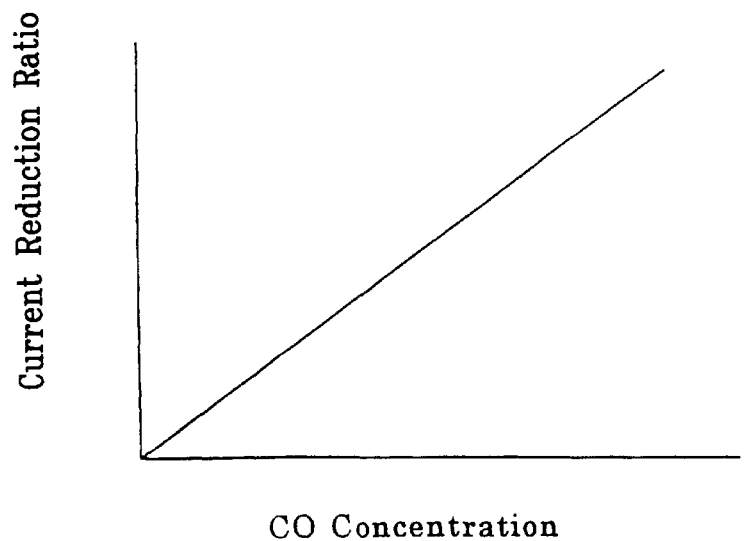
FIG. 13 is a graph which shows an analytical curve of the CO concentration rate with respect to the current reduction ratio when a CO oxidation potential and a CO adsorption potential are applied in a pulse like manner.

The method using a general purpose analytical curve is a general analytical method which uses the analytical curve obtained by the pulse method. In this connection, FIG. 12 is a graph which shows changes in the responsive current with lapse of time when a CO oxidation potential and a CO adsorption potential are applied in a pulse like manner. The principle of the pulse method is shown in FIG. 12. As shown in the drawing, in the pulse method, when a pulse potential having such a characteristic that is held at a CO oxidation potential for a certain period and then it is held at a CO adsorption potential for a certain period and then they are repeated are applied, the responsive current changes with lapse of time such that the responsive current decreases from a point of time when the applied potential is lowered from the CO oxidation potential to the CO adsorption potential. Therefore, from the ratio of the reduction (decrease) in this responsive current to the original current, an analytical curve of the CO concentration with respect to the current reduction ratio as shown in FIG. 13 is obtained, and then the CO concentration is measured based on the analytical curve thus obtained.

In FIG. 12, the electric current reduction ratio $\Delta\Theta_2$ can be calculated from the electric current value $I_o$ at time $t_o$ and the electric current value $I_2$ at time $t_2$ by using the following Equation 4.

Electric Current $$\text{Reduction Ratio: } \Delta\Theta_2 = (I_o - I_2)/I_o \quad \text{(Equation 4)}$$

However, in the case of a relatively high concentration of CO, the changes in the reduction in the responsive electric current becomes small, which in turn lowers the detection accuracy. In such a case, a measurement is carried out for the range of FIG. 12 where the responsive current decreases so as to have a large slope, and then the current reduction rate is obtained based on Equation 5 below. In this case, the electric current reduction ratio $\Delta\Theta_1$ can be calculated from the electric current value $I_o$ at time $t_o$ and the electric current value $I_1$ at time $t_1$.

Electric Current $$\text{Reduction Ratio: } \Delta\Theta_1 = (I_o - I_1)/I_o \quad \text{(Equation 5)}$$

In this way, because the thus obtained electric current reduction ratio ($\Delta\Theta_1$ or $\Delta\Theta_2$) depends on the CO concentration, data for the electric current reduction rate with respect to the CO concentration can be used as an analytical curve. In comparison with a continuous potential scanning method such as the cyclic voltammogram of the first embodiment, the method for applying potential in a pulse like manner according to the second embodiment has an advantage that can measure the concentration of CO even when the gas diffusion rate in the gas diffusion layer is faster, and this in turn makes it possible to shorten the response time to several tens of seconds to several seconds.

Now, if Equation 4 and Equation 5 are used to calculate the electric current reduction ratio for a region containing a low concentration of CO, the corresponding decrease in the responsive electric current will be small, thus leading to a small electric current reduction ratio and a high degree of error in the quantitative of CO. In such case, the degree of quantitative error can be made small by extending the CO adsorption potential holding time to make the amount of the responsive current reduction large.

Next, the measurement method will be described based on the actual measurement values.

Figure 14:
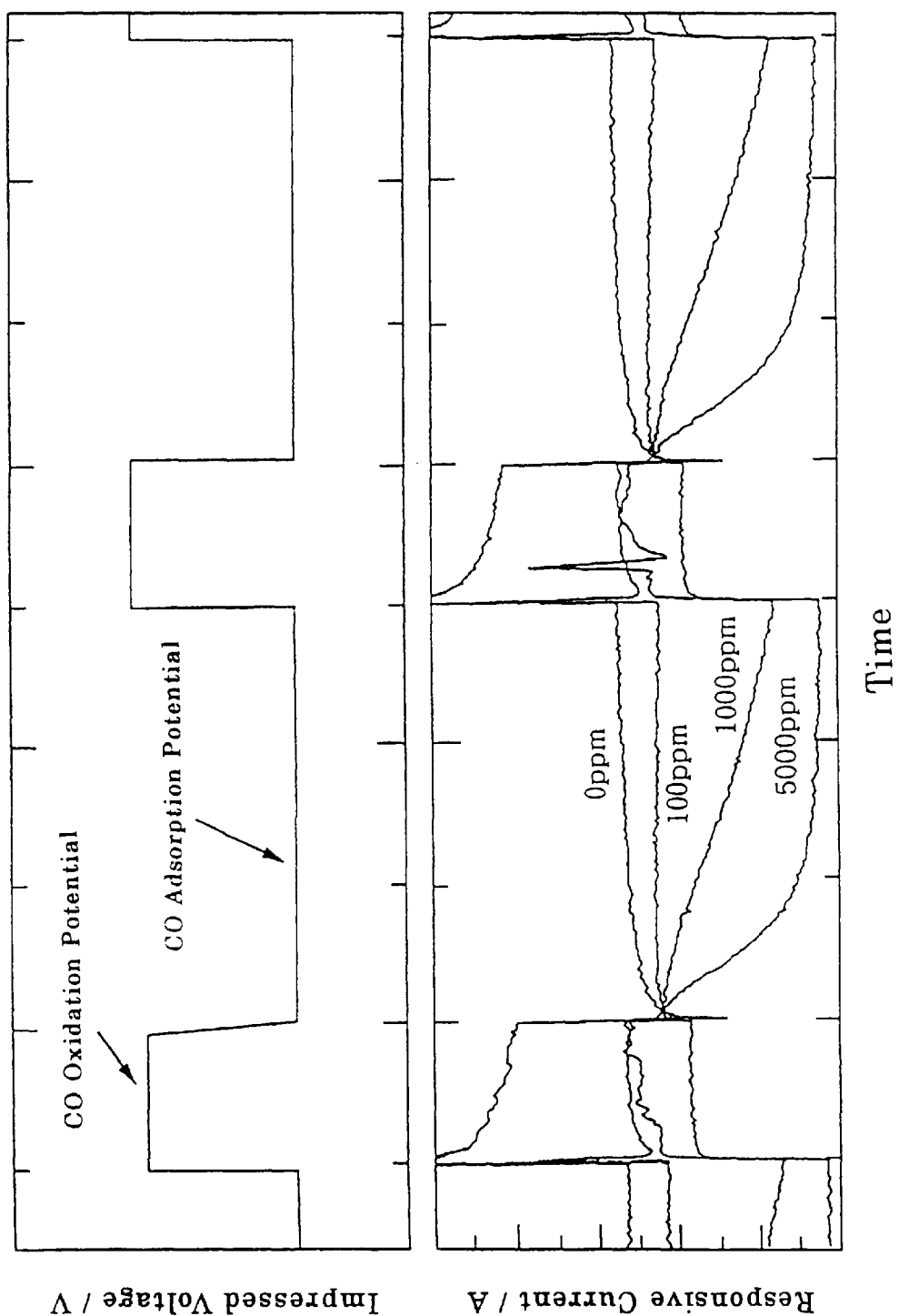
FIG. 14 is a graph which shows changes of the applied voltages and corresponding changes in the responsive currents obtained under the various CO concentration rates with elapse of time, which are obtained in an the experiment for studying changes of the responsive current when a CO oxidation potential and a CO adsorption potential are applied in a pulse like manner.
Figure 15:
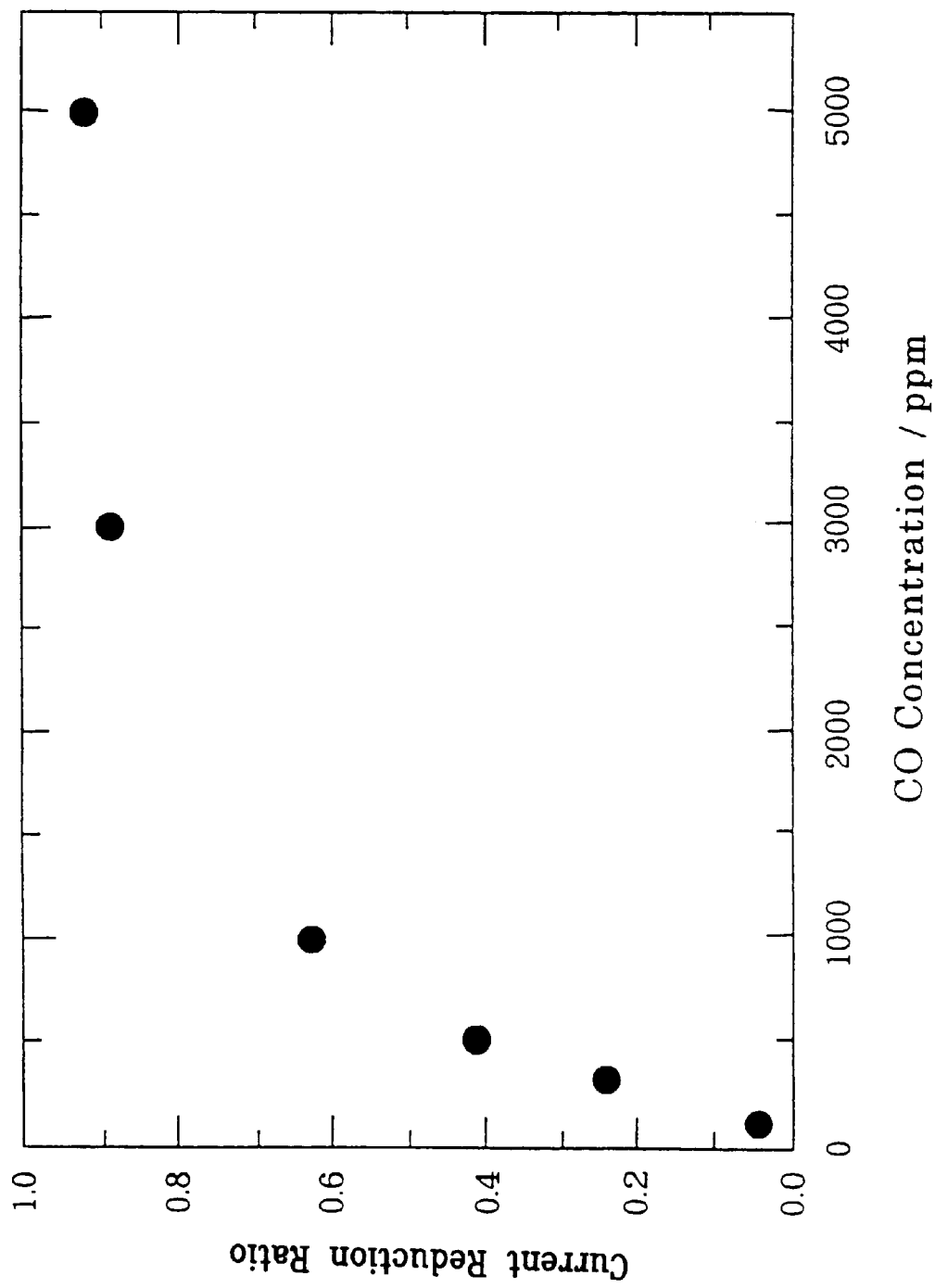
FIG. 15 is a graph which shows an analytical curve which is represented by plotting the current reduction ratio on the vertical axis and the CO concentration on the horizontal axis when a CO oxidation potential and a CO adsorption potential are applied in a pulse like manner.

The actual responsive electric current was measured for the respective CO concentration atmospheres in the case where a CO oxidation potential and a CO adsorption potential are applied in a pulse like manner. These results are shown by the graph of FIG. 14, in which the responsive electric current is plotted on the vertical axis and elapsed time is plotted on the horizontal axis. These graphs show that the decrease in the ionization current of hydrogen at the CO adsorption potential is dependent on the CO concentration. Further, based on these results, another analytical curve has been obtained, in which the electric current reduction ratio is plotted on the vertical axis and the CO concentration is plotted on the horizontal axis to show the relationship between the electric current reduction ratio and the concentration of CO. This is shown in FIG. 15.

Figure 16:
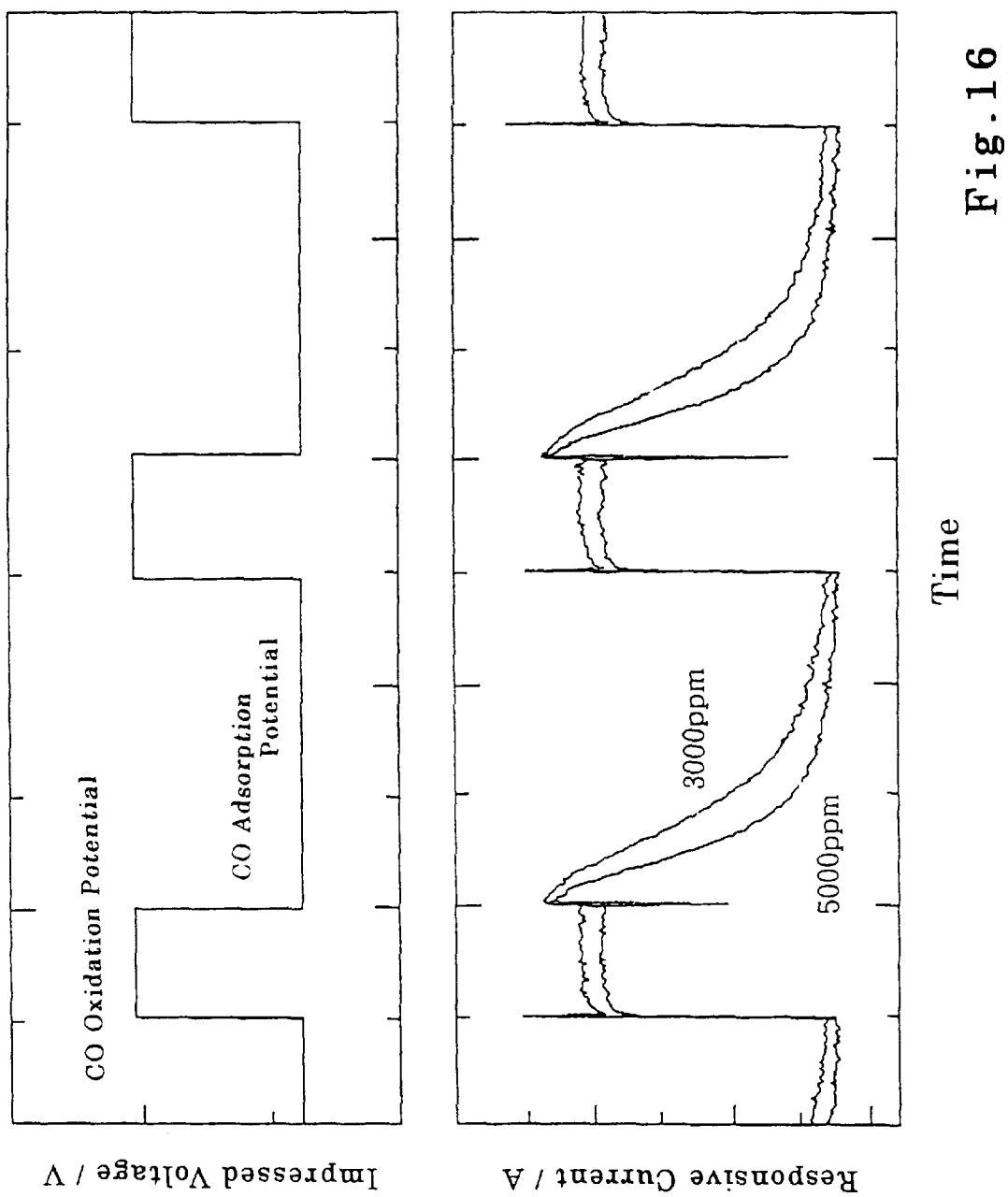
FIG. 16 is a graph which shows changes in the responsive current with elapse of time when the CO concentration is relatively high, that is 5000 ppm and 3000 ppm.

FIG. 16 is a graph which shows changes in the responsive electric current with elapse of time for the cases where the concentration of CO is relatively high, that is the concentration of CO is 5000 ppm and 3000 ppm, respectively. As shown in FIG. 16, when the concentration of CO is high, the difference in the reduction of the responsive electric current becomes small due to the saturation of CO adsorption coverage at high concentration levels, and this lowers the detection accuracy. In such a case, as was explained above, the electric current reduction ratio is calculated from Equation 5.

Figure 17:
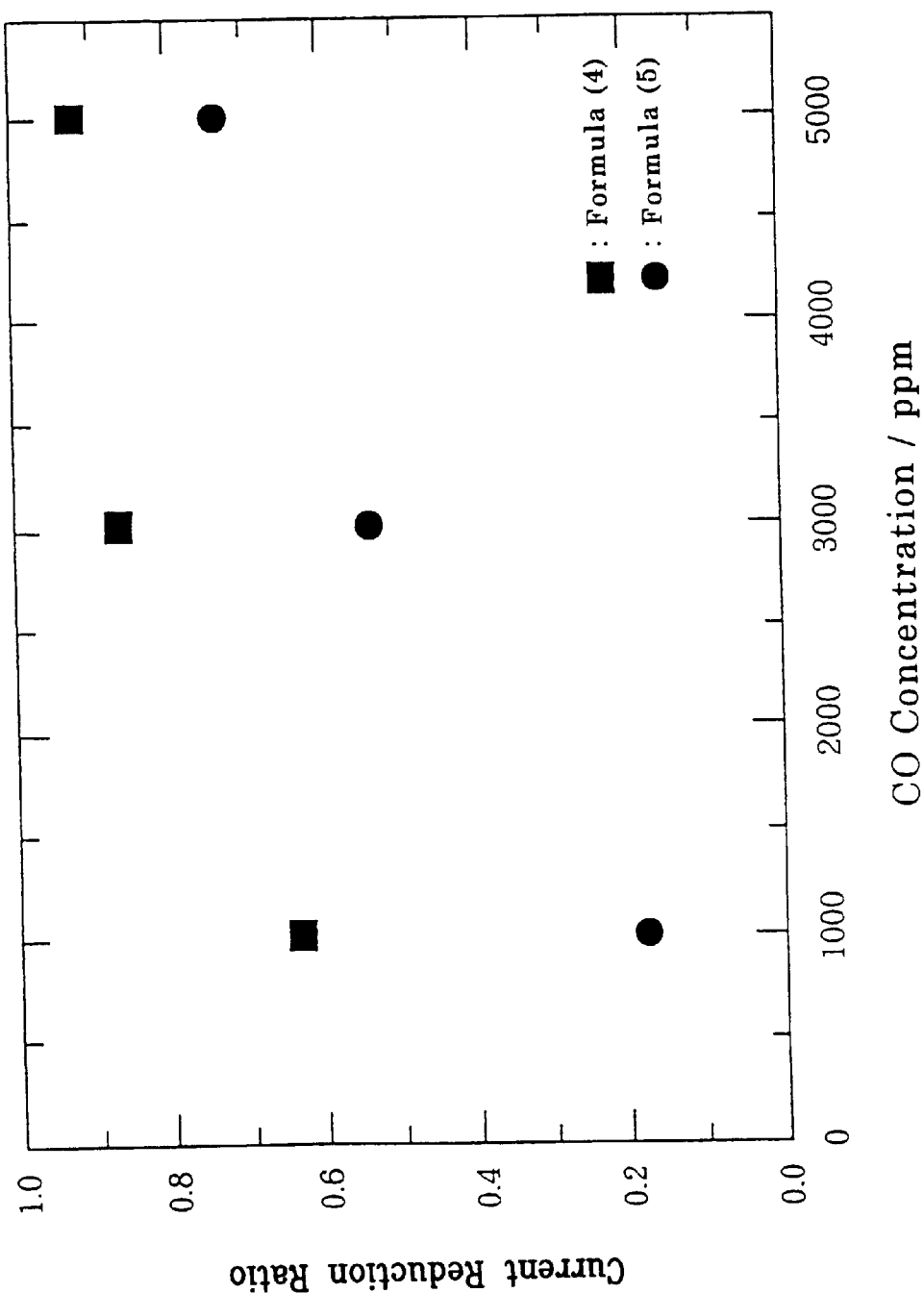
FIG. 17 is a graph which shows analytical curves which are represented by plotting the current reduction ratio on the vertical axis and the CO concentration on the horizontal axis when the CO concentration is relatively high.

In such case where the concentration of CO is high, an analytical curve which shows the relationship between the the electric current reduction ratio and the concentration of CO is shown in FIG. 17, in which the electric current reduction ratio is plotted on the vertical axis and the concentration of CO is plotted on the horizontal axis. In FIG. 17, the mark ● indicates the case in which the concentration of CO in the measured gas is high and therefore Equation 5 is applicable. As a comparison, the mark ■ indicates the case in which the concentration of CO is low and therefore Equation 4 is applicable. As shown in FIG. 17, the analytical curve obtained according to Equation 5 has a large slope over the high concentration region and therefore improves the measurement accuracy. Based on these analytical curves, the CO gas concentration measurement method according to the pulse method of the present invention makes it possible to determine a measured gas by the CO gas sensor and then to know the concentration of CO gas in the measured gas from the obtained electric current reduction ratio, and in this way the present invention makes it possible to measure the CO concentration in atmospheric conditions ranging from a relatively low concentration of CO to a relatively high concentration of CO.

Compared with the cyclic voltammetry method, the pulse method of measuring the concentration of CO according to the present invention requires a shorter responsive time for the responsive electric current, which not only shortens the measurement time, but also shortens the analysis time up until the measurement curve is obtained.

When carrying out a reforming process using methanol as a source material to manufacture a hydrogenous gas rich reformed gas, unreformed methanol vapor is present as an impurity at a concentration level of several percent in the reformed gas in addition to CO. As a result, when the detection electrode is held at the CO adsorption potential, the detection electrode adsorbs such methanol vapor in the same way it adsorbs the CO gas, thereby hindering the ionization of hydrogen and preventing the detection of CO. In this regard, the CO gas sensor and the CO gas concentration measurement method of the present invention which uses the pulse method utilizes the relatively slow adsorption speed of methanol in comparison to the adsorption speed of CO, so that by setting the optimum CO adsorption voltage holding time, it is possible to avoid interference from methanol.

2. Method Using Langmuir Type CO Adsorption Analytical Curve

The method using general purpose analytical curve described above 1. can be widely used for general purposes since the analytical method can be applied without any particular limitation for a CO potential pressure (adsorption rate) or a time domain. On the other hand, however, there is a disadvantage that it is necessary to determine whether either of Formula (4) or Formula (5) should be applied for the case where the CO concentration is high or low since the analytical curve of this method does not become linear in many cases. However, in the method using the Langmuir type CO adsorption analytical curve, it is possible to make the obtained analytical curve linear.

Figure 19:
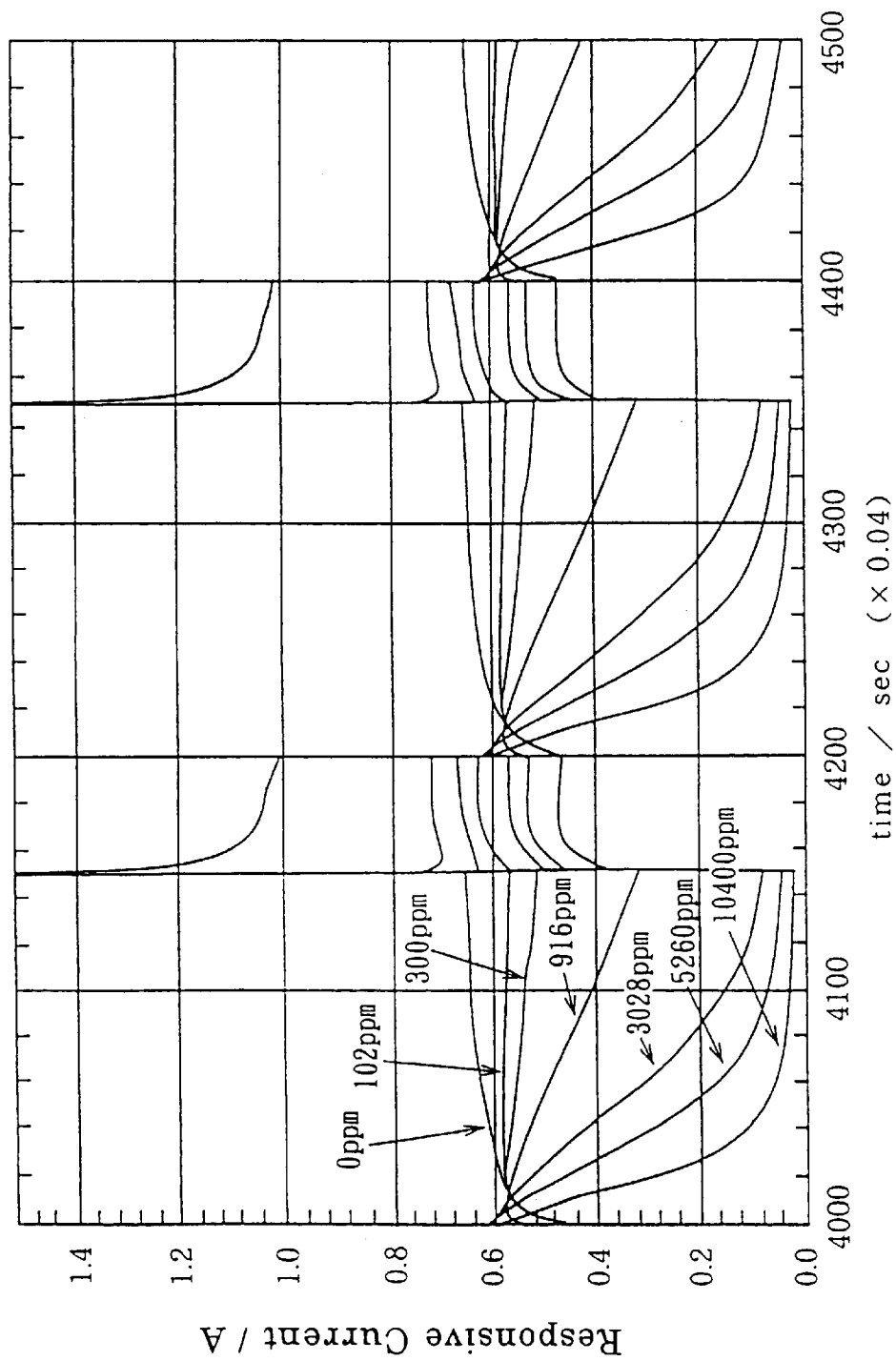
FIG. 19 is a graph which shows the data obtained by the pulse method, in which the responsive current (i) is plotted on the vertical axis and the elapsed time (t) is plotted on the horizontal axis for respective atmospheres having different CO concentrations according to the pulse method.

FIG. 19 relates to a measurement in which the actual responsive currents in the respective CO concentration atmospheres (10400 ppm, 5260 ppm, 3028 ppm, 916 ppm, 300 ppm, 102 ppm, 0 ppm) are measured under the condition that the CO oxidation potential (1.0 V) is applied for 2 seconds and then the CO adsorption potential (0.4 V) is applied for 6 seconds in a pulse like manner and then they are repeated at 80° C. under 1 atmospheric pressure. The results of the measurement is shown in FIG. 19, in which the responsive current (i) is plotted on the vertical axis and the elapsed time (t) is plotted on the horizontal axis.

Figure 18:
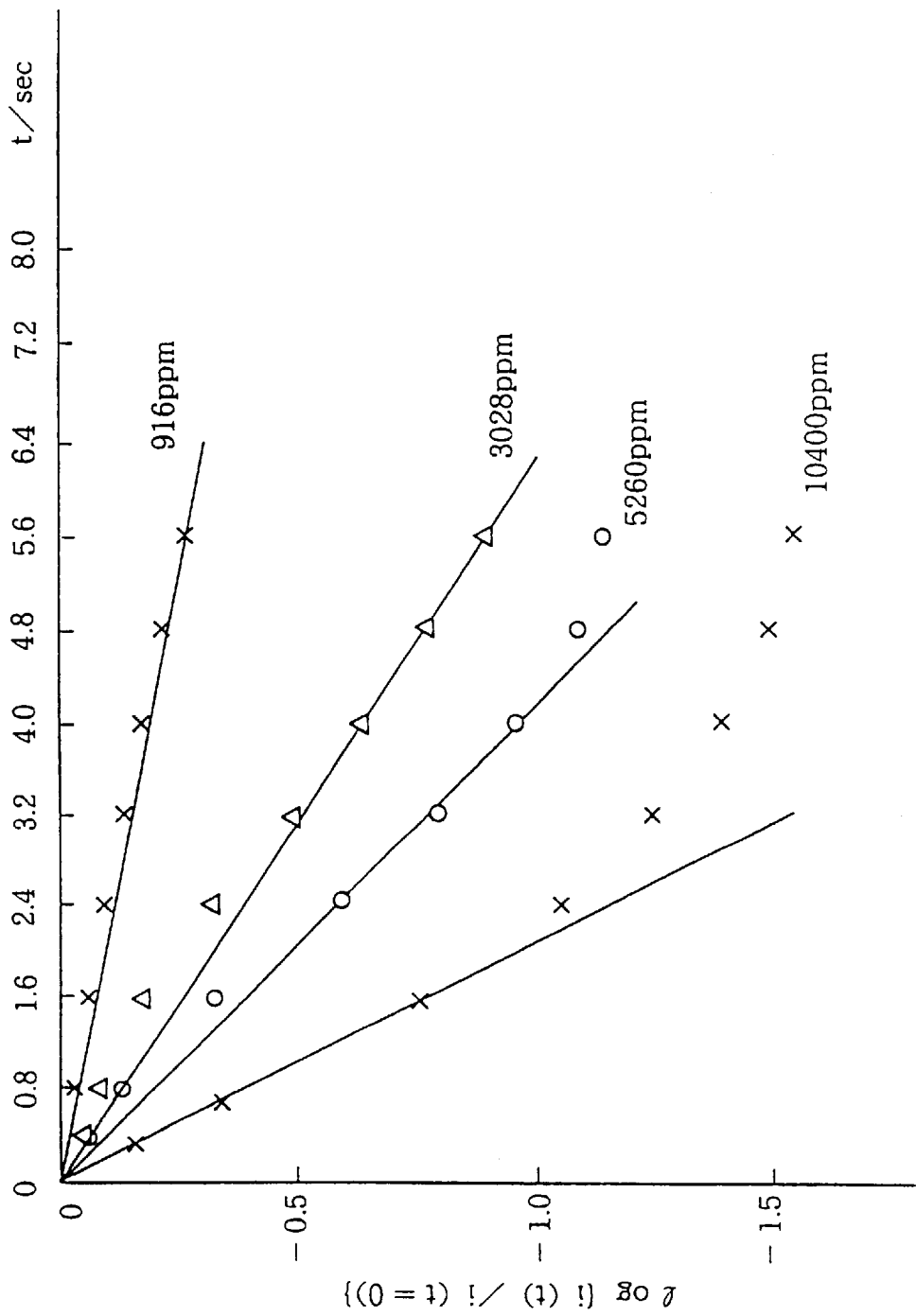
FIG. 18 is a graph which shows the data obtained by the pulse method, in which the elapsed time (t) is plotted on the horizontal axis and the natural logarithm of the ratio of the responsive current value at the respective elapsed time (t) with respect to the initial value [i(t=0)] of the responsive current is plotted on the vertical axis for respective atmospheres having different CO concentrations.

FIG. 18 is a graph for the respective CO concentration atmospheres, which is produced based on the results of FIG. 19, in which the elapsed time (t) is plotted on the horizontal axis and natural logarithm of the ratio of the responsive current value at the respective elapsed time (t) with respect to the initial value of the responsive current [i(t=0)] is plotted on the vertical axis. (In this connection, please note that the data in which the CO gas concentrations are 102 ppm and 300 ppm is eliminated.) As shown in the graph in FIG. 18, a time region in which the current reduction rate is not large shows a linear characteristic. Namely, even if the CO concentration is low or high, the CO adsorption coverage is small at the initial phase of the current reduction, and if there is no mutual interaction between the absorbed CO, the changes in the current show the Langmuir type curve. In this case, the following Formula (5) is established.

$$\ln \{i(t)/i(t=0)\} = -A \times P_{co} \times t \qquad \text{(Formula (6))}$$

(Here, A is a constant value, and Pco is a partial pressure of the CO gas)

In this way, at a time region where the current reduction rate is not large and in other word at a region where the CO adsorption coverage is not large, a linear relationship represented by the Formula (6) is established, and in this case the slope of the curve of this region is proportional to the CO concentration.

Figure 20:
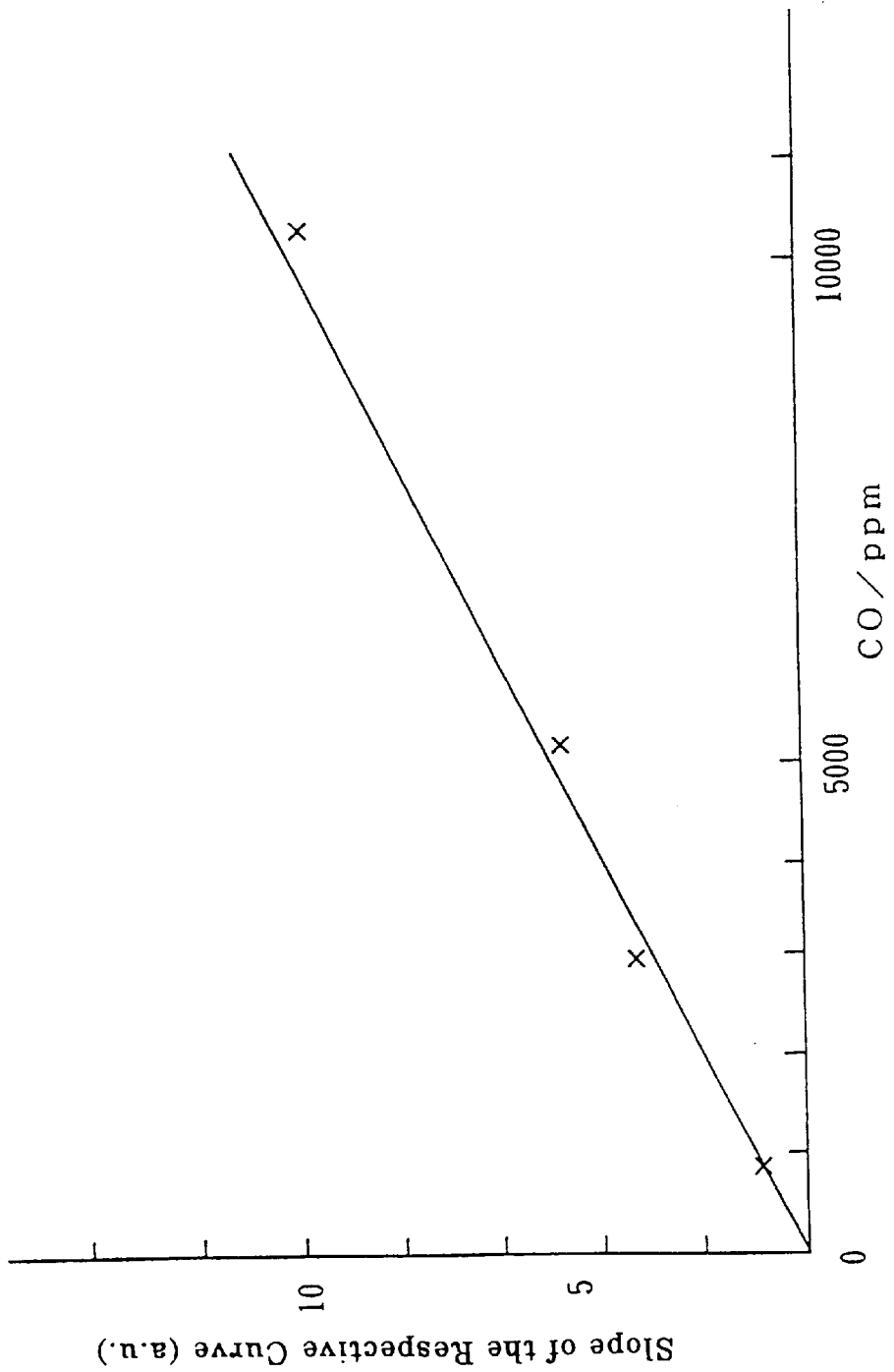
FIG. 20 is a graph which shows one example of an analytical curve obtained from FIG. 18 by the Langmuir-type CO adsorption analysis.

For example, FIG. 20 shows one example of the analytical curves according to the Langmuir type CO adsorption method. As shown in FIG. 20, the slope in the linear region shown in FIG. 18 becomes roughly proportional to the CO concentration, and it become linear.

(3) Method Using Analytical Curve Obtained based on the Relationship between the CO Concentration and the Inverse of the Time Required for Reaching a Predetermined Electric Current Reduction Rate The method using an analytical curve obtained based on the relationship between the CO concentration and the inverse of the time required for reaching a predetermined electric current reduction rate is capable of linearizing the analytical curve in the same way as the analytical method described above 2..

Figure 21:
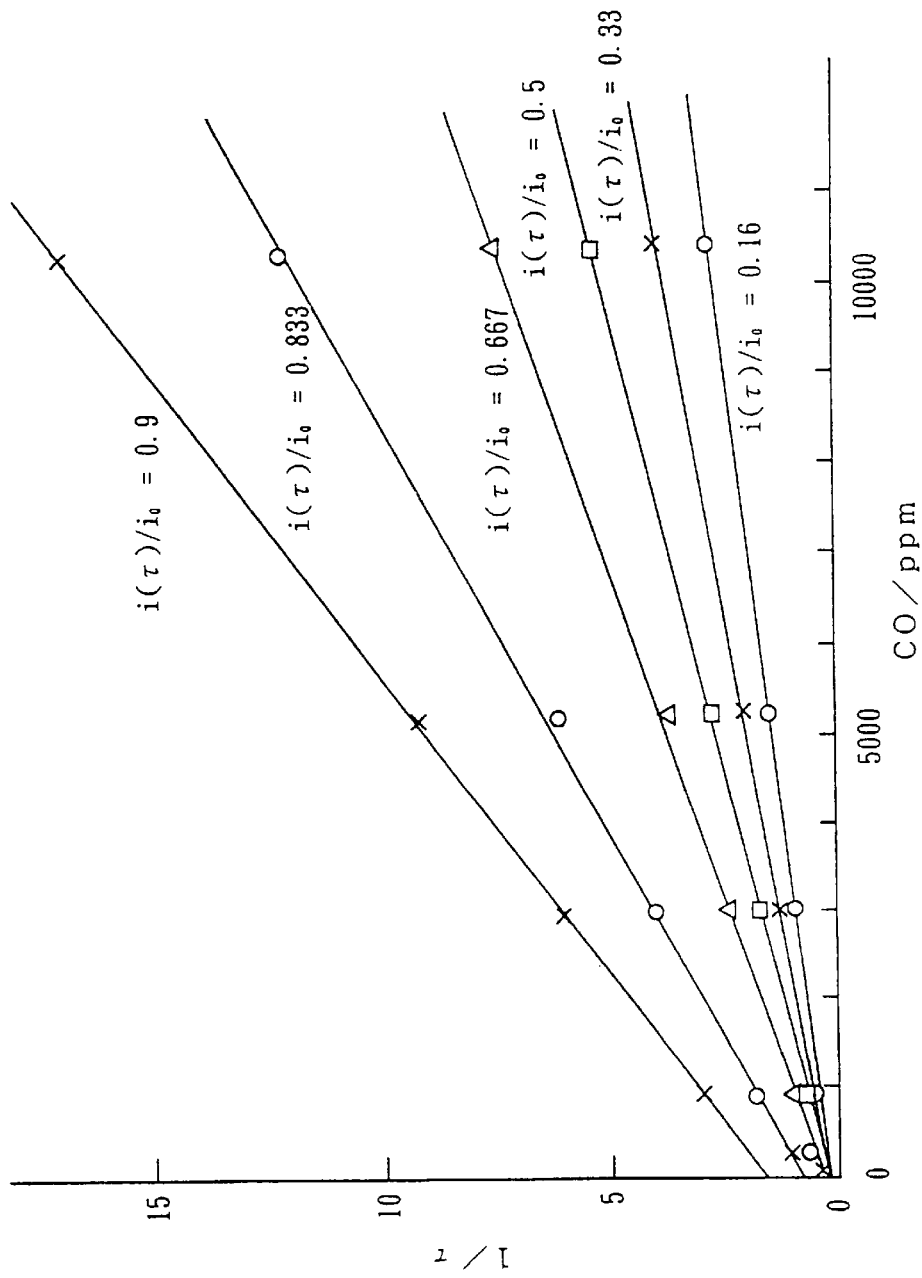
FIG. 21 is a graph obtained according to the pulsed method, which is represented by plotting the inverse number of the time ($\tau$) required for the current reduction ratio to reach a predetermined value on the vertical axis and the CO concentration (ppm) on the horizontal axis.

FIG. 21 is a graph which shows the respective current reduction ratio $\{i(\tau)/i(t=0)\}$, in which the inverse of time $\tau$ which is a time required for reaching a predetermined current reduction ratio is plotted on the vertical axis and the CO concentration is plotted on the horizontal axis. According to FIG. 21, the graph representing the respective electric current reduction ratio $\{i(\tau)/i(t=0)\}$ becomes linear. Namely, the inverse $(1/\tau)$ of time $\tau$ which is a time required for the current reduction ratio to reach a predetermined value is proportional to the CO concentration.

Therefore, by modifying Formula (6) by introducing time $\tau$ which is a time required for the current reduction ratio to reach a predetermined value, the inverse of time $\tau$ $(1/\tau)$ becomes the relationship shown by the following Formula (7).

$$1/\tau = -[A/\ln\{i(\tau)/i(t=0)\}] \times Pco \qquad \text{Formula (7)}$$

As shown in FIG. 21, the curves in the graph which represent the respective electric current reduction rates become linear. Although these curves should pass the origin, but they do not pass the origin in the region of the smaller electrical current reduction rate. It is believed that this is because the reading difference upon reading out the data from the original data shown in FIG. 19 is large particularly in the time region in which the current reduction ratio $\{i(\tau)/i(t=0)\}$ is relatively small.

(4) Method Using Analytical Curves Obtained from the Relationship between the CO concentration and the Electric Current Reduction Speed A method using analytical curves obtained from the relationship between the CO concentration and the electric current reduction speed is capable of obtaining linear analytical curves in the same way as the method 2. described above.

Figure 22:
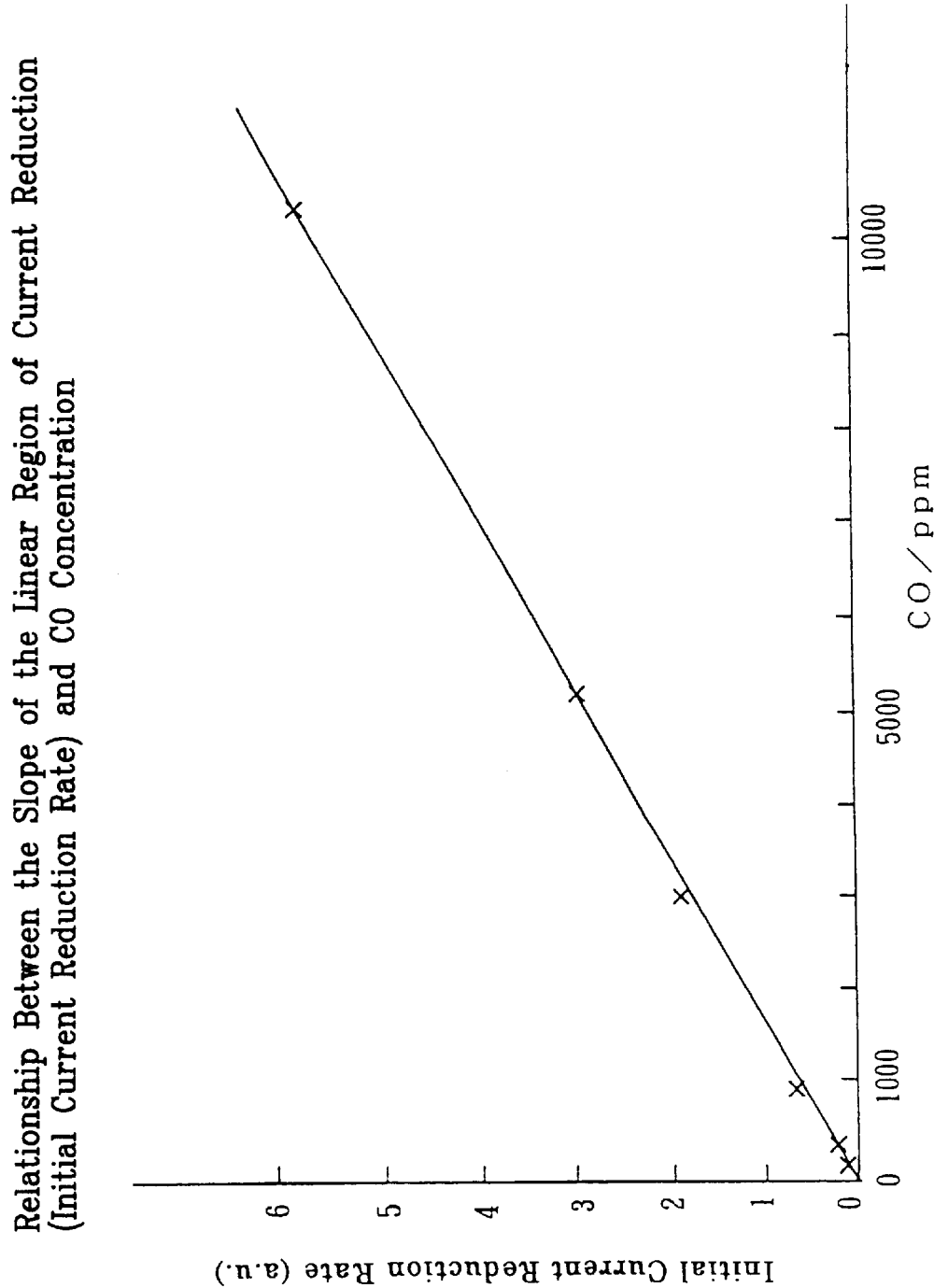
FIG. 22 is a graph in which the initial current reduction rate with respect to the CO concentration is shown for the region where the a current is reduced linearly with elapse of time at the initial stage of the current reduction.

According to FIG. 19 described above, there is a region in which the current is reduced linearly with elapse of time at the initial stage of the current reduction. The region can be represented with the graph shown in FIG. 22 in which the initial current reduction speed is plotted on the vertical axis and the CO concentration is plotted on the horizontal axis. As seen from the graph shown in FIG. 22, the current is linearly reduced with elapse of time, and its slope is proportional to the CO partial pressure (CO concentration).

Therefore, at the region where the CO partial pressure is low or at the initial stage of the current reduction, the following Formula (8) is established based on Formula (6) described above.

$$i(t)/i(t=0) = 1 - A \times Pco \times t \qquad \text{Formula (8)}$$

Methods using the analytical curves described in the above (1)–(4) for determining the CO concentrations according to the pulse method of the embodiment 2 can be selectively used depending on a range of the CO concentration and a region of time to be observed, so that they are capable of quntitatively measuring a tiny amount of CO in a large amount of hydrogen, carbon oxide gas and methanol (generally, organic flammable gas).

In the CO gas concentration measuring methods using either the cyclic voltammetry method or the pulse method, a CO gas is adhered to the counter electrode. Therefore, it is necessary to eliminate the adhered CO gas periodically. In the case of the detection electrode, the adhered CO gas can be eliminated from the electrode by inverting the potential. This means that in the same manner as the detection electrode, it is possible to revitalize the surface of the electrode by applying inverted potential to the counter electrode, thereby improving the durability of the CO gas sensor.

INDUSTRIAL UTILIZATION

According to the CO gas sensor and method of measuring the CO gas concentration of the present invention, it is possible to accurately carry out detection (qualitative analysis) and measurement (quantitative analysis) of the concentration of CO gas when CO gas is detected or measured in a gaseous atmosphere containing a relatively large amount of hydrogen gas without interference from the hydrogenous gas.

If an electrolyte used in the CO gas sensor of the present invention is formed from a solid polymer electrolyte membrane, a responsive time becomes shortened in comparison with the case where the aqueous electrolyte is used, thereby obtaining a CO concentration value in a short time.

The principle of the CO gas sensor and method of measuring the CO gas concentration according to the present invention can be applied not only to a quantitative measurement of CO but also a quantitative measurement of $CO_2$ in a reforming gas. Namely, by switching a holding potential, it is possible to carry out control for $CO_2$ concentration in a reforming gas in addition to the CO concentration.

Further, according to the CO gas sensor and method of measuring the CO gas concentration, it is possible to carry out a measurement of CO gas over the wide range from the low concentration to the high concentration.

Furthermore, the CO gas censor of the present invention according to the cyclic voltammetry method or the pulse method can be also used as a gas sensor for detecting CO in a high concentration hydrogenous atmosphere such as a reformed natural gas or the like in addition to a gas sensor for detecting CO in a fuel gas for fuel cells.

What is claimed is:

1. A method for detecting CO concentration in a gas containing CO and hydrogen in an amount in excess of the CO, said method comprising:

providing a CO gas sensor including a detection electrode, a counter electrode and an electrolyte interposed between the detection electrode and the counter electrode;

contacting the gas with the detection and counter electrodes;

impressing voltages on said electrodes, while in contact with said gas, to obtain a change of hydrogen ionization current corresponding to CO adsorption by said detection electrode; and determining the change in hydrogen ionization current as a measure of CO concentration in the gas.

2. A method according to claim 1 wherein the determined change is a decrease in hydrogen ionization current due to adsorption CO by the detection electrode.

3. A method according to claim 2 wherein said decrease in hydrogen ionization current is measured for a predetermined period of time at a voltage producing CO adsorption by the detection electrode.

4. A method according to claim 2 wherein the determined change is determined as a period of time elapsed in reaching a predetermined fraction of an initial hydrogen ionization current.

5. A method according to claim 1 wherein said determining includes generation of a cyclic voltammogram.

6. A method according to claim 5 wherein the CO gas sensor further includes an electrolyte solution with the electrodes immersed therein in a spaced relationship, wherein said contacting includes saturating the electrolyte with the gas, and wherein the hydrogen ionization current is allowed to stabilize at each voltage and then determined.

7. A method according to claim 5 wherein the electrodes are in a container, wherein said contacting is by introducing the gas into the container and wherein said determining is conducted after the concentration of CO in the gas within the container has stabilized.

8. A method according to claim 1 wherein the imposed voltage is a pulsed voltage.

9. A method according to claim 8 wherein the change is determined as a period of time required to reach a predetermined fraction of an initial hydrogen ionization current and wherein the determination of CO concentration is made by applying the determined period of time to a, analytical curve for a relationship between CO concentration and the inverse of the time required to reach the predetermined fraction after initiation of hydrogen ionization current.

10. A method according to claim 8 wherein said determining is by applying a ratio of a hydrogen ionization current at time t to a hydrogen ionization current at time O to a langmuir analytical graph for CO adsorption.

11. A method according to claim 8 wherein said determining includes determination of a ratio of the detected decrease in the hydrogen ionization current to an initial hydrogen ionization current and applying the determined ratio to an analytical graph for a relationship between the CO concentration and ratios of decrease in hydrogen ionization current to initial hydrogen ionization current.

12. A method according to claim 8 wherein said determining includes determination of an initial speed of decrease in hydrogen ionization current and applying the determined speed to a predetermined plot of initial speeds of decrease in hydrogen ionization current versus CO concentration.

13. A method according to claim 1 wherein said gas is a reforming gas.

14. A method according to claim 1 wherein the imposed voltage is set to avoid reduction of $CO_2$.

15. A method according to claim 1 comprising imposing a first voltage which produces a first hydrogen ionization current without adsorption of CO and a second voltage which produces adsorption of CO by the detection electrode and a second hydrogen ionization current less than said first hydrogen ionization current, and wherein said change is a difference between said first and second hydrogen ionization currents.

16. A method according to claim 1 wherein the impressed voltage is a pulsed voltage which varies between a CO oxidation potential and a CO adsorption potential.

* * * * *

UNITED STATES PATENT AND TRADEMARK OFFICE
CERTIFICATE OF CORRECTION

PATENT NO. : 6,090,268
DATED : July 18, 2000
INVENTOR(S) : KUNIMATSU et al

It is certified that error appears in the above-identified patent and that said Letters Patent is hereby corrected as shown below:

Col. 1, line 38, "for" should read --in--;
    line 63, delete "by the present"; and
    line 64, delete "inventors, the inventors have found a CO gas".
Col. 2, line 16, "impressing" should read --impressed--.
Col. 3, line 31, "a methanol" should read --methanol--; and
    line 58, "concentration rates" should read --concentrations--.
Col. 4, line 43, after "gas is" insert --passed--.
Col. 6, line 39, "long" should read --a long--.
Col. 7, line 1, after "electricity" insert --produced--; and "adsorbed hydrogen" should read --hydrogen adsorption--.
Col. 10, line 28, "repeated are" should read --repeatedly--.
Col. 11, line 1, "that" should read --that it--.
Col. 12, line 42, "is" should read --are--; and
    line 66, "rate" should read --ratio--.
Col. 13, line 8, "become" should read --is--;
    line 16, "rate" should read --ratio--; and
    line 39, delete "but".

UNITED STATES PATENT AND TRADEMARK OFFICE
CERTIFICATE OF CORRECTION

PATENT NO. : 6,090,268
DATED : July 18, 2000
INVENTOR(S) : KUNIMATSU et al

It is certified that error appears in the above-identified patent and that said Letters Patent is hereby corrected as shown below:

Col. 15, line 3, "adsorption" should read --adsorption of--;
line 31, "a," should read --an--.

Signed and Sealed this

Twenty-second Day of May, 2001

Attest:

NICHOLAS P. GODICI

*Attesting Officer*    Acting Director of the United States Patent and Trademark Office